(12) United States Patent
Elkins et al.

(10) Patent No.: US 7,993,325 B2
(45) Date of Patent: Aug. 9, 2011

(54) RENAL INFUSION SYSTEMS AND METHODS

(75) Inventors: Jeffrey M. Elkins, Novato, CA (US); Harry B Goodson, IV, Fremont, CA (US); Craig A Ball, San Carlos, CA (US); Aurelio Valencia, East Palo Alto, CA (US); Samir R Patel, Mountain View, CA (US); Neema Hekmat, Mountain View, CA (US)

(73) Assignee: Angio Dynamics, Inc., Latham, NY (US)

( * ) Notice: Subject to any disclaimer, the term of this patent is extended or adjusted under 35 U.S.C. 154(b) by 87 days.

(21) Appl. No.: 11/241,749

(22) Filed: Sep. 29, 2005

(65) Prior Publication Data
US 2006/0079859 A1 Apr. 13, 2006

Related U.S. Application Data

(63) Continuation-in-part of application No. PCT/US03/29740, filed on Sep. 22, 2003, and a
(Continued)

(51) Int. Cl.
*A61M 31/00* (2006.01)
(52) U.S. Cl. .................................. 604/508; 604/284
(58) Field of Classification Search .......... 604/101.01, 604/101.03, 101.05, 102.01, 43–45, 258, 604/276, 508, 510, 523, 284
See application file for complete search history.

(56) References Cited

U.S. PATENT DOCUMENTS
1,696,018 A 12/1928 Schellberg
(Continued)

FOREIGN PATENT DOCUMENTS
DE 4324637 A1 7/1993
(Continued)

OTHER PUBLICATIONS

Madyoon et al., "Fenoldopam for prevention of contrast-induced renal dysfunction in a high risk angiography population: A historically-controlled case series", Circulation vol. 104, No. Suppl. 17, XP009098219, Oct. 23, 2001, p. II-185.
(Continued)

*Primary Examiner* — Theodore Stigell
*Assistant Examiner* — Kami A Bosworth
(74) *Attorney, Agent, or Firm* — Peter J. Flora

(57) ABSTRACT

Systems, devices, and methods for delivering treatment to the renal arteries are provided. Exemplary systems include a delivery catheter having a distal bifurcation, an introducer assembly comprising an introducer sheath in operative association with a Y-hub, wherein Y-hub includes a first port for receiving the delivery catheter and a second port for receiving a second catheter, and a constraint assembly for holding the distal bifurcation of the delivery catheter in a low-profile configuration when it is advanced distally beyond the introducer sheath.

11 Claims, 19 Drawing Sheets

Related U.S. Application Data continuation-in-part of application No. PCT/US2004/008571, filed on Mar. 19, 2004, and a continuation-in-part of application No. 11/084,738, filed on Mar. 16, 2005, now Pat. No. 7,914,503, which is a continuation-in-part of application No. PCT/US03/29744, filed on Sep. 22, 2003, and a continuation-in-part of application No. 11/084,434, filed on Mar. 18, 2005, now Pat. No. 7,364,566, which is a continuation of application No. PCT/US03/29995, filed on Sep. 22, 2003, and a continuation-in-part of application No. 11/083,802, filed on Mar. 18, 2005, which is a continuation of application No. PCT/US03/29743, filed on Sep. 22, 2003, and a continuation-in-part of application No. 11/084,295, filed on Mar. 18, 2005, now Pat. No. 6,994,700, which is a continuation of application No. PCT/US03/29585, filed on Sep. 22, 2003, and a continuation-in-part of application No. PCT/US2004/008573, filed on Mar. 19, 2004, and a continuation-in-part of application No. 11/073,421, filed on Mar. 4, 2005, and a continuation-in-part of application No. 11/129,101, filed on May 13, 2005, now Pat. No. 7,585,836.

(60) Provisional application No. 60/508,751, filed on Oct. 2, 2003, provisional application No. 60/476,347, filed on Jun. 5, 2003, provisional application No. 60/502,600, filed on Sep. 13, 2003, provisional application No. 60/412,343, filed on Sep. 20, 2002, provisional application No. 60/412,476, filed on Sep. 20, 2002, provisional application No. 60/479,329, filed on Jun. 17, 2003, provisional application No. 60/502,389, filed on Sep. 13, 2003, provisional application No. 60/486,349, filed on Jul. 10, 2003, provisional application No. 60/486,206, filed on Jul. 9, 2003, provisional application No. 60/502,399, filed on Sep. 13, 2003, provisional application No. 60/505,281, filed on Sep. 22, 2003, provisional application No. 60/543,671, filed on Feb. 9, 2004, provisional application No. 60/550,632, filed on Mar. 4, 2004, provisional application No. 60/550,774, filed on Mar. 5, 2004, provisional application No. 60/571,057, filed on May 14, 2004, provisional application No. 60/612,731, filed on Sep. 24, 2004, provisional application No. 60/612,801, filed on Sep. 24, 2004.

(56) References Cited

U.S. PATENT DOCUMENTS

| | | | |
|---|---|---|---|
| 2,499,045 A | | 2/1950 | Walker et al. |
| 3,144,868 A | | 8/1964 | Jascalevich |
| 3,455,298 A | | 7/1969 | Anstadt |
| 3,516,408 A | | 6/1970 | Montanti |
| 3,667,069 A | | 6/1972 | Blackshear et al. |
| 3,730,186 A | | 5/1973 | Edmunds, Jr. et al. |
| 3,791,374 A | | 2/1974 | Guarino |
| 3,841,331 A | | 10/1974 | Wilder et al. |
| 3,995,623 A | | 12/1976 | Blake et al. |
| 4,248,224 A | * | 2/1981 | Jones ............................ 604/284 |
| 4,309,994 A | | 1/1982 | Grunwald |
| 4,345,602 A | | 8/1982 | Yoshimura et al. |
| 4,407,271 A | | 10/1983 | Schiff |
| 4,423,725 A | | 1/1984 | Baran et al. |
| 4,459,977 A | | 7/1984 | Pizon et al. |
| 4,490,374 A | | 12/1984 | Bandurco et al. |
| 4,493,697 A | | 1/1985 | Krause et al. |
| 4,536,893 A | | 8/1985 | Parravicini |
| 4,546,759 A | | 10/1985 | Solar |
| 4,554,284 A | | 11/1985 | Stringer et al. |
| 4,636,195 A | | 1/1987 | Wolinsky |
| 4,685,446 A | | 8/1987 | Choy |
| 4,705,502 A | | 11/1987 | Patel |
| 4,705,507 A | | 11/1987 | Boyles |
| 4,712,551 A | | 12/1987 | Rayhanabad |
| 4,714,460 A | | 12/1987 | Calderon |
| 4,723,939 A | | 2/1988 | Anaise |
| 4,753,221 A | | 6/1988 | Kensey et al. |
| 4,781,716 A | | 11/1988 | Richelsoph |
| 4,817,586 A | | 4/1989 | Wampler |
| 4,834,707 A | | 5/1989 | Evans |
| 4,840,172 A | | 6/1989 | Augustine et al. |
| 4,846,831 A | | 7/1989 | Skillin |
| 4,861,330 A | | 8/1989 | Voss |
| 4,863,461 A | | 9/1989 | Jarvik |
| 4,888,011 A | | 12/1989 | Kung et al. |
| 4,902,272 A | | 2/1990 | Milder et al. |
| 4,902,291 A | | 2/1990 | Kolff |
| 4,906,229 A | | 3/1990 | Wampler |
| 4,909,252 A | | 3/1990 | Goldberger |
| 4,911,163 A | | 3/1990 | Fina |
| 4,919,647 A | | 4/1990 | Nash |
| 4,925,377 A | | 5/1990 | Inacio et al. |
| 4,925,443 A | | 5/1990 | Heilman et al. |
| 4,927,407 A | | 5/1990 | Dorman |
| 4,927,412 A | | 5/1990 | Menasche |
| 4,938,766 A | | 7/1990 | Jarvik |
| 4,950,226 A | | 8/1990 | Barron |
| 4,957,477 A | | 9/1990 | Lundback |
| 4,964,864 A | | 10/1990 | Summers et al. |
| 4,976,691 A | | 12/1990 | Sahota |
| 4,976,692 A | | 12/1990 | Atad |
| 4,990,139 A | | 2/1991 | Jang |
| 4,995,864 A | | 2/1991 | Bartholomew et al. |
| 5,002,531 A | | 3/1991 | Bonzel |
| 5,002,532 A | | 3/1991 | Gaiser et al. |
| 5,044,369 A | | 9/1991 | Sahota |
| 5,053,023 A | | 10/1991 | Martin |
| 5,059,178 A | | 10/1991 | Ya |
| 5,067,960 A | | 11/1991 | Grandjean |
| 5,069,662 A | | 12/1991 | Bodden |
| 5,069,680 A | | 12/1991 | Grandjean |
| 5,073,094 A | | 12/1991 | Dorman et al. |
| 5,087,244 A | * | 2/1992 | Wolinsky et al. ........ 604/103.01 |
| 5,089,019 A | | 2/1992 | Grandjean |
| 5,098,370 A | | 3/1992 | Rahat et al. |
| 5,098,442 A | | 3/1992 | Grandjean |
| 5,112,301 A | | 5/1992 | Fenton, Jr. et al. |
| 5,112,349 A | | 5/1992 | Summers et al. |
| 5,119,804 A | | 6/1992 | Anstadt |
| 5,129,883 A | | 7/1992 | Black |
| 5,131,905 A | | 7/1992 | Grooters |
| 5,135,474 A | | 8/1992 | Swan et al. |
| 5,158,540 A | | 10/1992 | Wijay et al. |
| 5,160,323 A | | 11/1992 | Andrew |
| 5,163,910 A | | 11/1992 | Schwartz et al. |
| 5,167,628 A | | 12/1992 | Boyles |
| 5,180,364 A | | 1/1993 | Ginsburg |
| 5,205,810 A | | 4/1993 | Guiraudon et al. |
| 5,226,888 A | | 7/1993 | Arney |
| 5,256,141 A | | 10/1993 | Gencheff et al. |
| 5,257,974 A | | 11/1993 | Cox |
| 5,282,784 A | | 2/1994 | Willard |
| 5,290,227 A | | 3/1994 | Pasque |
| 5,292,309 A | * | 3/1994 | Van Tassel et al. ............ 604/117 |
| 5,308,319 A | | 5/1994 | Ide et al. |
| 5,308,320 A | | 5/1994 | Safar et al. |
| 5,312,343 A | | 5/1994 | Krog et al. |
| 5,320,604 A | | 6/1994 | Walker et al. |
| 5,326,374 A | | 7/1994 | Ilbawi et al. |
| 5,328,470 A | | 7/1994 | Nabel et al. |
| 5,332,403 A | | 7/1994 | Kolff |
| 5,345,927 A | | 9/1994 | Bonutti |
| 5,358,519 A | | 10/1994 | Grandjean |
| 5,364,337 A | | 11/1994 | Guiraudon et al. |
| 5,370,617 A | | 12/1994 | Sahota |
| 5,383,840 A | | 1/1995 | Heilman et al. |
| 5,397,307 A | | 3/1995 | Goodin |
| 5,411,479 A | | 5/1995 | Bodden |

| | | |
|---|---|---|
| 5,421,826 A | 6/1995 | Crocker et al. |
| 5,429,584 A | 7/1995 | Chiu |
| 5,453,084 A | 9/1995 | Moses |
| 5,464,449 A | 11/1995 | Ryan et al. |
| 5,476,453 A | 12/1995 | Mehta |
| 5,478,331 A | 12/1995 | Heflin et al. |
| 5,484,385 A | 1/1996 | Rishton |
| 5,505,701 A | 4/1996 | Anaya Fernandez de Lomana |
| 5,509,428 A | 4/1996 | Dunlop |
| 5,536,250 A | 7/1996 | Klein et al. |
| 5,558,617 A | 9/1996 | Heilman et al. |
| 5,569,296 A | 10/1996 | Marin et al. |
| 5,599,306 A | 2/1997 | Klein et al. |
| 5,609,628 A | 3/1997 | Keranen |
| 5,613,949 A | 3/1997 | Miraki |
| 5,613,980 A | 3/1997 | Chauhan |
| 5,617,878 A | 4/1997 | Taheri |
| 5,643,171 A | 7/1997 | Bradshaw et al. |
| 5,643,215 A | 7/1997 | Fuhrman et al. |
| 5,669,924 A | 9/1997 | Shaknovich |
| 5,702,343 A | 12/1997 | Alferness |
| 5,713,853 A | 2/1998 | Clark et al. |
| 5,713,860 A | 2/1998 | Kaplan et al. |
| 5,720,735 A * | 2/1998 | Dorros ............ 604/284 |
| 5,755,779 A | 5/1998 | Horiguchi |
| 5,762,599 A | 6/1998 | Sohn |
| 5,766,151 A | 6/1998 | Valley et al. |
| 5,776,190 A | 7/1998 | Jarvik |
| 5,797,876 A | 8/1998 | Spears et al. |
| 5,807,311 A | 9/1998 | Palestrant |
| 5,807,895 A | 9/1998 | Stratton et al. |
| 5,817,046 A | 10/1998 | Glickman |
| 5,902,229 A | 5/1999 | Tsitlik et al. |
| 5,902,336 A | 5/1999 | Mishkin |
| 5,913,852 A | 6/1999 | Magram |
| 5,928,132 A | 7/1999 | Leschinsky |
| 5,935,924 A | 8/1999 | Bunting et al. |
| 5,968,013 A | 10/1999 | Smith et al. |
| 5,971,910 A | 10/1999 | Tsitlik et al. |
| 5,984,955 A | 11/1999 | Wisselink |
| 6,001,079 A | 12/1999 | Pourchez |
| 6,013,054 A | 1/2000 | Jiun Yan |
| 6,039,721 A | 3/2000 | Johnson et al. |
| 6,068,629 A | 5/2000 | Haissaguerre et al. |
| 6,077,256 A | 6/2000 | Mann |
| 6,086,527 A | 7/2000 | Talpade |
| 6,086,557 A * | 7/2000 | Morejohn et al. ......... 604/96.01 |
| 6,096,073 A | 8/2000 | Webster et al. |
| 6,117,117 A * | 9/2000 | Mauch ............ 604/103 |
| 6,117,156 A | 9/2000 | Richter et al. |
| 6,142,973 A | 11/2000 | Carleton et al. |
| 6,143,002 A | 11/2000 | Vietmeier |
| 6,156,016 A | 12/2000 | Maginot |
| 6,165,120 A | 12/2000 | Scheich, Jr. et al. |
| 6,190,349 B1 | 2/2001 | Ash et al. |
| 6,210,380 B1 | 4/2001 | Mauch |
| 6,251,133 B1 | 6/2001 | Richter et al. |
| 6,261,273 B1 | 7/2001 | Ruiz |
| 6,261,316 B1 * | 7/2001 | Shaolian et al. ............ 623/1.11 |
| 6,287,277 B1 | 9/2001 | Yan |
| 6,287,608 B1 * | 9/2001 | Levin et al. ............... 424/718 |
| 6,325,826 B1 | 12/2001 | Vardi et al. |
| 6,387,037 B1 | 5/2002 | Boiling et al. |
| 6,390,969 B1 | 5/2002 | Boiling et al. |
| 6,468,241 B1 | 10/2002 | Gelfand et al. |
| 6,475,208 B2 | 11/2002 | Mauch |
| 6,482,211 B1 | 11/2002 | Choi |
| 6,494,875 B1 | 12/2002 | Mauch |
| 6,508,787 B2 | 1/2003 | Erbel et al. |
| 6,514,226 B1 | 2/2003 | Levin et al. |
| 6,533,747 B1 | 3/2003 | Polschegg et al. |
| 6,540,779 B2 | 4/2003 | Richter et al. |
| 6,544,219 B2 * | 4/2003 | Happ et al. .................. 604/284 |
| 6,592,567 B1 | 7/2003 | Levin et al. |
| 6,595,959 B1 | 7/2003 | Statienko et al. |
| 6,669,718 B2 | 12/2003 | Besselink |
| 6,699,231 B1 | 3/2004 | Sterman et al. |
| 6,733,474 B2 | 5/2004 | Kusleika |
| 6,749,598 B1 | 6/2004 | Keren et al. |
| 6,749,628 B1 | 6/2004 | Callol et al. |
| 6,884,258 B2 | 4/2005 | Vardi et al. |
| 6,887,258 B2 | 5/2005 | Denison et al. |
| 6,911,039 B2 | 6/2005 | Shiu et al. |
| 6,945,992 B2 | 9/2005 | Goodson et al. |
| 6,994,700 B2 | 2/2006 | Elkins et al. |
| 7,104,981 B2 | 9/2006 | Elkins et al. |
| 7,381,204 B2 | 6/2008 | Wilson et al. |
| 7,470,252 B2 | 12/2008 | Mickley et al. |
| 2001/0029349 A1 | 10/2001 | Leschinsky |
| 2001/0031907 A1 | 10/2001 | Downey et al. |
| 2002/0022857 A1 | 2/2002 | Goldsteen et al. |
| 2002/0090388 A1 | 7/2002 | Humes et al. |
| 2002/0091355 A1 | 7/2002 | Hayden |
| 2002/0165574 A1 | 11/2002 | Ressemann et al. |
| 2002/0169413 A1 | 11/2002 | Keren et al. |
| 2003/0050600 A1 | 3/2003 | Ressemann et al. |
| 2003/0069468 A1 | 4/2003 | Bolling et al. |
| 2003/0100919 A1 | 5/2003 | Hopkins et al. |
| 2003/0144636 A1 | 7/2003 | Liu |
| 2003/0153898 A1 | 8/2003 | Schon et al. |
| 2003/0181856 A1 | 9/2003 | Goldman |
| 2003/0220664 A1 | 11/2003 | Petrick et al. |
| 2004/0002730 A1 | 1/2004 | Denison et al. |
| 2004/0044302 A1 | 3/2004 | Bernard et al. |
| 2004/0064089 A1 | 4/2004 | Kesten et al. |
| 2004/0097900 A1 | 5/2004 | Keren et al. |
| 2004/0111148 A1 | 6/2004 | Goodson |
| 2004/0117003 A1 | 6/2004 | Ouriel et al. |
| 2004/0167463 A1 | 8/2004 | Zawacki et al. |
| 2005/0027305 A1 | 2/2005 | Shiu et al. |
| 2005/0197624 A1 | 9/2005 | Goodson et al. |
| 2005/0245882 A1 | 11/2005 | Elkins et al. |
| 2005/0245892 A1 | 11/2005 | Elkins et al. |
| 2005/0267010 A1 | 12/2005 | Goodson et al. |
| 2006/0030814 A1 | 2/2006 | Valencia et al. |
| 2006/0036218 A1 | 2/2006 | Goodson et al. |
| 2006/0047266 A1 | 3/2006 | Elkins et al. |
| 2006/0069323 A1 | 3/2006 | Elkins et al. |
| 2006/0079836 A1 | 4/2006 | Holman et al. |
| 2006/0079859 A1 | 4/2006 | Elkins et al. |
| 2006/0149350 A1 | 7/2006 | Patel et al. |
| 2006/0259066 A1 | 11/2006 | Euteneuer |

FOREIGN PATENT DOCUMENTS

| | | |
|---|---|---|
| EP | 654283 A1 | 11/1994 |
| EP | 884064 A2 | 5/1998 |
| GB | 2239675 A | 7/1994 |
| WO | WO 97/11737 | 4/1997 |
| WO | WO 98/03213 A1 | 1/1998 |
| WO | WO 98/17347 A1 | 4/1998 |
| WO | WO 98/52639 A1 | 11/1998 |
| WO | WO 99/33407 A1 | 12/1998 |
| WO | WO 99/22784 A1 | 5/1999 |
| WO | WO 99/51286 A1 | 10/1999 |
| WO | WO 00/41612 A2 | 1/2000 |
| WO | WO 01/83016 | 4/2001 |
| WO | WO 01/37882 A | 5/2001 |
| WO | WO 01/41861 A1 | 6/2001 |
| WO | WO 01/97687 | 12/2001 |
| WO | WO 01/97717 | 12/2001 |
| WO | WO 01/97878 A1 | 12/2001 |
| WO | WO 01/97879 A1 | 12/2001 |
| WO | WO 2004/026370 A | 4/2004 |
| WO | WO 2004/032791 A | 4/2004 |
| WO | WO 2005/002660 A1 | 1/2005 |
| WO | WO 2005/014100 A1 | 2/2005 |

OTHER PUBLICATIONS

Mathur, V.S., "Pathophysiology of radiocontrast nephropathy and use of fenoldopam for its prevention", Reviews in Cardiovascular Medicine, vol. 2, No. Suppl. 1, 2001, pp. 54-58, XP009098238.

Stone, G.W. et al., "Design and rationale of CONTRAST—a prospective, randomized, placebo-controlled trial of fenoldopam mesylate for the prevention of radiocontrast nephropathy", Reviews in Cardiovascular Medicine, vol. 2, No. Suppl.1, 2001, pp. 531-536, XP009098217.

Tumlin et al., "A multicenter, double-blind, placebo-controlled trial of fenoldopam meysylate in the prevention of radiocontrast nephropathy in patients with moderate to severe renal insufficiency" Journal of the American Society of Nephrology, Vo. 11, Sep. 2000, p. 135A, XP009098223.

Tumlin, J.A. et al., Fenoldopam mesylate blocks reductions in renal plasma flow after radiocontrast dye infustion: a pilot trial in the prevention of contrast nephropathy:, Americal Heart Jouornal, vol. 143, No. 5, May 2002, pp. 894-903, XP002475379.

"Chronic Renal Insufficiency," downloaded from internet website http://www.nutropin.com/patient/5_1_renal_insifficiency.jsp, retrieved on Nov. 13, 2006.

"Diabetes Mellitus," University of Maryland Medical Center webpage, retrieved from http://www.umm.edu/altmed/ConsConditions/DiabetesMellituscc.html on Nov. 13, 2006.

"FDA Form 510(K) on Related Correspondence for Advanced Equipment Development, Inc."

Agostoni et al. Sustained Benefit from Ultrafiltration in Moderate Congestive heart failure Cardiology 2001:96 183-189.

Akaba, N. et al.; "A Cylinder-Shaped Balloon Catheter for the Management of Dissecting Aneurysms in Acute Stage," Herz, vol. 17, No. 6, pp. 390-393, Dec. 1992. Abstract Only.

Aspelin, et al., "Nephrotoxic Effects in High-Risk Patients Undergoing Angiography," N Engl J Med, Feb. 2003, vol. 348, No. 6, pp. 491-499.

Bakris, et al., Renal Hemodynamics in Radiocontrast Medium-Induced Renal Dysfunction etc. Kidney International, vol. 56 pp. 206-210 (1999).

Beregi, et al., "Doppler Flow Wire Evaluation of Renal Blood Flow Reserve in Hyertenstive Patient With Normal Renal Arteries," *Cardiovascular and Interventional Radiology*, vol. 23, pp. 340-346 (2000).

Bergey, E.A. et al.; "Transhepatic Insertion of Vascular Dialysis Catheters in Children: A Safe, Life-Prolonging Procedure," Pediatr. Radiol., vol. 29, No. 1, pp. 42-50, Jan. 1999. Abstract Only.

Bischoff, W. et al.; "Modified in Suty Perfusion of the Kidney Using Balloon Catheters," vol. 94, No. 30, pp. 1695-1697, Oct. 21, 1976. Abstract Only.

Briguori et al., "Contrast Agent-Associated Nephrotoxicity," Progress in Cardiovascular Diseases, 45;6(2003): 493-503.

Canaud, B. et al.; "Temporary Vascular Access for Extracorporeal Renal Replacement Therapies in Acute Renal Failure Patients," Kidney Int. Suppl., vol. 66, pp. S142-S150, May 1998. Abstract Only.

Chatterjee, "Refractory heart failure-drugs and devices", *European Heart Journal*, 2001, 22:2227-2230.

Chu, et al. "Fenoldopam in the Prevention of Contrast Media-Induced Acute Renal Failure," *The Annals of Pharmacotherapy*, 35:1278-1282 (2001).

Cohn, Jay N.; "The Management of Chronic Heart Failure," The New England Journal of Medicine, pp. 490-498. Aug. 15, 1996.

Darves, "ASHP: Perioperative Fenoldopam Improves Renal Function During Major Surgery," Retrieved from the Internet [Online]: www.pslgroup.com/dg/225C72.htm, Dec. 19, 2002.

Del Greco, The Kidney in Congestive Heart Failure, Modern Concepts of Cardiovascular, Sep. 1975, vol. 44, No. 9, pp. 47-52.

D'Elia, et al., Nephrotoxicity from Angiographic Contrast Material, "A prospective Study," Am J Med, May 1982, vol. 72, pp. 719-725.

Diaz-Sandoval, et al., "Acetylcysteine to Prevent Angiography-Related Renal Tissue Injury," *The American Journal of Cardiology*, Feb. 1, 2002: vol. 89, pp. 356-358.

Drescher, et al., Prevention of Contrast Medium-Induced Renal Vasospasm by Phosphodiesterase Inhibition, Invest Radiol 1998; 33:858-862.

Eisenberg, et al., Renal Failure After Major Angiography Can be Avoided with Hydration, AJR, May 1981; 136:859-861.

Eisenberg, et al., Renal Failure After Major Angiography, Am J Med, Jan. 1980, vol. 68, pp. 43-46.

Eisenberger, F. et al.; "Transfemoral Cannulation of the Renal Vessels. Diagnostic and Therapeutic use in Urology," Urologe [A], vol. 16, No. 1, pp. 1-5, Jan. 1977. Abstract Only.

Elkayam, et al., Renal Hemodynaic Effects of Vasodilation with Nifedipine and -lydralazine in Patients With Heart Failure, JACC Dec. 1984; vol. 4, No. 6, pp. 1261-1267.

Elkayam, et al., Renal Vasodilatory Effect of Endothelial Stimulation in Patients with Chronic Congestive Heart Failure, J Am Coll Cardiol 1996;28:176-182.

Encarta dictionary, "Prevent," downloaded from website http://encarta.msn.com/encnet/features/dictionary/DictionaryResults.aspx?refid=1861737040, 2007, 1 page, retrieved Apr. 18, 2007.

Farncombe, "Dyspnea: assessment and treatment," Support Care Cancer, 1997, 5, 94-99.

Fox, S.L.; "Mechanisms of Contraction," Human Physiology, Fourth Edition, pp. 300-323.

Freeman, et al., "Nephropathy Requiring Dialysis After Percutaneous Coronary Intervention and the Critical role of an Adjusted Contrast Dose," *Am J Cardiol*, vol. 90, (Nov. 15, 2002) pp. 1068-1073.

Garwood, Susan et al.; "Renal Preservation Strategies for High Risk Patients,"University of Chico School Medicine, Cover Page, Table of Contents Page, pp. 1-19, 1998.

Geisburg et al., "Addressing the Challenges of Cardiorenal Syndrome," Cleveland Clinic Journal of Medicine, 2006, 73, 485-491.

Gerlach, et al., "Contrast Medium-induced Nephrotoxicity: Pathophysiology and Prevention," *Pharmacotherapy*, 2000, 20(5):540-548.

Gianello et al., Clinical Transplantation, 1995, 9, 481-489.

Greco, B.A. et al.; "Atherosclerotic Ischemic Renal Disease," Am. J. Kidney Dis., vol. 29, No. 2, pp. 167-187, Feb. 1997. Abstract Only.

Gruberg, et al. The prognostic implications of further renal deterioration within 48 h of interventional etc. J AM Coll Cardiol 2000, 20(5):540-548.

Halpenny et al. The effects of fendolopam on renal blood flow and tubular function during aortic cross-clamping in anaesthetized dogs, EUR J Anaestestheisol, Aug. 2000: 17(8); 491-8 Abstract.

Heyman, et al., Pathophysiology of Radiocontract Nephropathy, A Role for Medullary Hypoxia, Invest Radiol, 1999; 34:685-691.

Hobbs, et al., "An Update on Nesiritide for Treatment of Decompensated Heart Failure," *Exp. Opin. Invest. Drugs*, 2001, 10(5):935-942.

Houghton, et al., "Basal and Reserve Renal Artery Blood Flow: Effect of Endothelium-Dependent and Independent Vasoactive Agonist and Radiographic Contrast Medium in Two Patients", *J invas Cardiol* 2000, 12: 211-215.

Hunter et al., "Preventing Contrast-Induced Nephropathy with Fenoldopam," Techniques in Vascular and Interventional Radiology. 2001. 4:1:53-56.

Iannone, L.D. et al.; "Effect of Primary Balloon Expandable Renal Artery Stents o Long-Term Patency, Renal Function, and Blood Pressure in Hypertensive and Renal Insufficient Patient with Renal Artery Stenosis," Cathet. Cardiovasc. Dign., vol. 37, No. 3, pp. 243-250, Mar. 1996. Abstract Only.

Jacobs, M.J. et al.; "Reduced Renal Failure Following Thoracoabdominal Aortic Aneurysm Repair by Selective Prefusion," Eur. J. Cardiothorac. Surg., vol. 14, No. 2, pp. 201-205, Aug. 1998. Abstract Only.

Katsumata T. et al. "Newly-Developed Catheter for Cardio-Renal Assist During Intraaortic Balloon Counterpulsation," Kyobu Geka, vol. 46, No. 9, pp. 767-770, Aug. 1993. Abstract Only.

Kay, et al., Acetylcysteine for Prevention of Acute Deterioration of Renal Function Following Elective Coronary Angiography and Intervention, *JAMA*, vol. 289 No. 5, (Feb. 5, 2003).

Kehrer et al.; "Construction and Experimental Application of a Catheter for Selective Arterial Kidney Perfusion in Situ," Urological Research, vol. 13, pp. 85-89, 1985.

Kim, et al., Flouriscopic Landmarks for Optimal Visualization of the Proximal Reral Arteries, JVIR, 10:37-39 (1999).

Kini et al. A protocol for Prevention of Radiographic contrast Nepropathy etc. Catheterization and Cardiovascular Interventions 2002, 55:169-173.

Kini et al. Managing the High-Risk Patient: Experience with Fenoldopam etc. Rev. Cardiovas Med 2001:2 (Suppl 1) S19-S25.

Kobayashi, A. et al.; "Experimental Study on the Usefulness of the Autoperfusion Balloon Catheter in Maintaining the Blood Supply to the Distal Organs," Nippon Igaku Hoshasen Gakkai Zasshi, vol. 52, No. 5, pp. 682-684, May 25, 1992. Abstract Only.

Kou-Gi Shyu et al., "Acetylcysteine Protects Against Acute Renal Damage in Patients with Abnormal Renal Function Undergoing a Coronary Procedure," The Journal of the American College of Cardiology, 2002; 40:8.

Lass, et al., Cardiocascular and Renal Hemodynamic Effects of Intravenous Infusions of the Selective DA1 Agonist ec., Circulation 1988; 78:1310-1315.

Levin, Howard, R. et al.; "Reversal of Chronic Ventricular Dilation in Patients with End-Stage Cardiomyopathy by Prolonged Mechanical Unloading," vol. 91, No. 11, pp. 2727-2748, Jun. 1, 1995.

Linden, R.J. et al.; "The Nature of the Atrial Receptors Responsible for a Reflex Decrease in Activity in Renal Nerves of the Dog," The Physiological Society, pp. 31-40, 1980.

Madyoon, "Clinical Experience with the Use of Fenoldopam for Prevention of Radiocontrast Hephropathy etc," Rev Cardiovasc Med. 2001, 2(suppl 1 ); S26-S30.

Madyoon, Use of Fenoldopam to Prevent Radiocontrast Nephropathy etc. Catheterization and Cardiovascular Interventions 2001, 53:341-345.

Margulies, et al., Induction and Prevention of Radiocontrast-Induced Nephropathy in Dogs with Heart Failure, Kidney Int. 1990; vol. 38:1101-1108.

Margulies, et al., Intra-Arterial Atrial Natriuetic Factor (ANF) Attenuates Radiocontrast-Induced etc., Renal Pathology, unknown date, pp. 666, Abstract only.

Masaki, Z. et al.; "In Situ Perfusion by Retrograde Cannulation of a Tumor Artery for Nephron-Sparing Surgery," Int. J. Urol, vol. 2, No. 3, pp. 161-165, Jul. 1995. Abstract Only.

Mason, et al., Renal Dysfunction After Arteriography, JAMA, 1985;253:1001-1004.

Mathis, J. M. et al.; "Use of Guide Catheter as a Temporary Stent During Microcatheter Intervention," AJNR Am. J. Neuroradiol, vol. 19, No. 5, pp. 932-933, May 1998. Abstract Only.

Mathur et al., The effects of fenoldopam, a selective dopamine receptor agonist, on renal hemodynamics etc. Abstract only. Crit Cre Med Sep. 1999; 27(9) 1832-1837.

Mathur, "The Role of the DA1 Receptor Agonist Fenoldopam in the Management of Critically Ill, Transplant, and Hypertensive Patients," Reviews in Cardiovascular Medicine, 2003;4(Supp 1):S35-S40.

Mccarthy, Animal Models in Medical Device Development and Qualification, Charles River Laboratories, vol. 10(2) 1997.

Mccullough, et al., Acute Renal Failure after Coronary Intervention: Incencence, Risk Factors, and Relationships to Mortality, Am J Med. 1997; 103:368-375.

Mehran, et al., "A Risk Score for Prediction of Contrast Induced nephropathy After Percutaneous Coronary Intervention," Retrieved from the Internet [Online]: www.abstractsonline.com/viewer, Mar. 31, 2003.

Mehran, et al., "Radiocontrast-Induced Acute Renal Failure: Allocations and Outcomes," Rev Cardiovasc Med 2001;2(suppl1):S9-S13.

Middleton, J. P.; "Ischemic Disease of the Kidney: How and Why to Consider Revascularization," J. Nephrol., vol. 11, No. 3, pp. 123-136, May-Jun. 1998. Abstract Only.

Miller, et al., "Effects of Fenoldopam on Renal Blood Flow and Tubular Function Following Supraerenal Aortic Cross-Clamping," Ann Vasc Surg, 2003, Published online Oct. 23, 2003. Abstract Only.

Mintz, et al., "Radiocontrast-Induced Nephropathy and Percutaneous Coronary Intervention," Expert Opin. Pharmacother., 2003; 4(5):639-652.

Mueller et al. Prevention of Contrast Media Associated Nephropathy, Arch Intern Med, Feb. 2002, vol. 162 pp. 329-336.

Murray et al., "Clinical Anesthesiology: Third Edition." McGraw-Hill Professional. New York. 2002.

Nohria et al. Medical Management of Advanced Heart Failure, JAMA, Feb. 6, 2002, vol. 162, pp. 628-640.

Novick, A.C.; "Atherosclerotic Ischemic Nephropathy. Epidemiology and Clinical Considerations,"Urol. Clin. North Am., vol. 21, No. 2, pp. 195-200, May 1994. Abstract Only.

Paganini, et al., "Severity Scores and Outcomes With Acute Renal Failure in the ICU Setting," Contrib Nephrol, 2001; 132:181-195.

Parfrey, et al., Contrast Material-Induced Renal Failure in Patients with Diabetes Mellitus, Renal Insufficiency, or Both, N Engl J Med, 1989, 320:149-153.

Patel, et al., Intravenous Fenoldopam Infusion in Severe Heart Failure, Cardiovasc Drugs Ther 1993; 7:97-101.

Pharmacy and Therapeutics Committee, Fenoldopam Mesylate (Corlopam) Usage Guidelines:, Clinical Pharmacy Associates, Inc. Feb. 2001. http://www.clinpharm.com/client_data/productfiles/fenoldopam%20usage%20guidelines.pdf Access Nov. 29, 2007.

Pierce, "Fenoldopam (Corlopam) DUE", Pharmacy & Therapeutics Committee, Jan. 2002, http://prodruginfo.com/Formulary/DUE/fenolddue.pdf, Accessed Sep. 12, 2007.

Postma, C.T. et al.; "Treatment of Renal Artery Stenosis with Intra-Arterial Stents," Ned Tijdshr Genneeskd., vol. 142, No. 39, pp. 2132-2137, Sep. 26, 1998. Abstract Only.

Ramanathan, et al., Ameliorating Contrast-Induced Nephropathy, Journal of Invasive Cardiology, Nov. 2001, Retrieved from the Internet [Online]: www.invasivecardiology.comlfic_20011/jic_200111f6.html.

Rebeiz, et al., "Radiocontrast Nephropathy: a Time for Affirmative Action, J Invasive Cardiology," Jan. 2003; vol. 15, No. 1, pp. 23-24.

Rihal, et al., "Incidence and Prognostic Importance of Acute Renal Failure After Percutaneous Coronary Intervention," Circulation, (May 14, 2002),105:2259-2264.

Ritchie, et al., "Use of nonionic or Low Osmolar Contrast Agents in Cardiovascular Procedures," Retrieved from the Internet [Online] www.acc.org/clinical/position/72543.htm, Jan. 22, 2003.

Robinson, et al., "Congestive Heart Failure: Targeted Drug Therapy and Invasive Interventions", Retrieved from the Internet [Online] www.speroff.com/articlesITextbook/66_CHF2.htm, printed Sep. 4, 2002.

Rudnick, et al., Nephrotoxicity of Ionic and Noionic Contrast Media in 1196 Patients: A Randomized Trial, Kidney International, 1995; 47:254-261.

Schwab, et al., Contrast Nephrotoxicity: A Randomized Controlled Trial of a Nonionic and an Ionic Radiographic Contrast Agent, N Engl J Med, 1989, 320:149-153.

Seiter, H. et al.; "Modified T-Catheter and its use for Transvenous Hypothermic in Situ Perfusion in the Surgical Restoration of the Kidney with staghorn calculi," Z. Uro Nephrol., vol. 76, No. 6, pp. 403-406, Jun. 1983. Abstract Only.

Sheifer, "Sex Differences in Coronary Atery Size", American Heart Journal, 2000; 139(4):649-653.

Shusterman, et al., Fenoldopam, But Not Nitroprusside, Improves Renal Function etc. Am J of Medicine, 95:161-168 (1993).

U.S. Appl. No. 09/165,333—Leschinsky, Boris—"Method and Apparatus for Treating Aneuryms".

Solomon, et al., Effects of Saline, Mannitol, and Furosemide on Acute Decreases in Renal Function etc., N Engl J Med 1994; vol. 331 No. 21 pp. 1416-1420.

Stevens, et al., A Prospective Randomized Trail of Prevention Measures in Patients at High Risk for Contrast Nephropathy, J Am Coll Cardiol, 1999; 33:403-411.

Strick, et al., Direct Measurement of Renal Medullary Blood Flow in the Dog, Am J. Physiol. 267 (Regulatory Integrative Comp. Physiol. 36): R253-R2259, 1994.

Suehiro, et al., "Selective Renal Vasodilation and Active Renal Artery Perfusion Improve Renal Function in Dogs with Acute Heart Failure," The Journal of Pharmacology and Experimental Therapeutics, vol. 298, No. 3 pp. 1154-1160 (2001).

Taliercio et al., Risks for Renal Dysfunction with Cardiac Angiography, Annals of Internal Medicine, 1986; 104:501-504.

Thatipelli et al., "CT Angiography of Renal Artery Anatomy for Evaluating Embolic Protection Devices." Journal of Vascular and Interventional Radiology. 2007; 18(7): 842-846.

Thomas, et al., Glomerrular Filtration Dynamics During Renal Vasodilation etc. Am. J. Physiol. 244:F606-F611 (1983).

Thomas, et al., Influence of Bradykinin and Papaverine on Renal etc., Renal Physiology, Basel 5:197-205 (1982).

Tumlin et al., "Fenoldopam Mesylate Blocks Reductions in Renal Plasma Flow After Radiocontrast Dye Infusion: A Pilot Trial in the Prevention of contrast Nephropathy," The American Heart Journal, 2002; 143:5:894-903.

UIC College of Pharmacy, "Is Fenoldopam (Corlopam) Useful for the Prevention of Contrast Media Associated Nephrotoxicity?", Retrieved from the Internet [Online] www.uic.edu/pharmacy/services/di/fenoldopam.htm, Jan. 2003.

Umrani et al., Beneficial effects of fenoldopam treatment on renal function in streptozotocin-induced diabetic rats, Clin Exp Hypertens, Apr. 24, 2002 (3): 207-19 Abstract only.

Van Der Zander et al., "Hypertension: Does Brain Natriuretic Paptide Have a Direct Renal Effect in Human Hypertensives?", American Heart Association, 2003, 41, 119-123.

Vari, et al., Induction, Prevention and Mechanisms of Contrast Media-Induced Acute Renal Failure, Kidney International, 1988; 33:669-707.

Venkatamaran, "Prevention of acute renal failure," Crit. Care Clin., 2005, 21(2), 281-289 (abstract).

Walker, H.S. et al.; "Use of a Balloon-Tipped Profusion Catheter for Renal Preservation During Suprarenal Abdominal Aortic Operations," J. Vasc. Surg., vol. 2. No. 2, pp. 337-339, Mar. 1985. Abstract Only.

Weisberg et al., Risk of radiocontrast nephropathy in patients with and without diabetes mellutus, Kidney International, 1994, 45:259-265.

White, C.J. et al.; "Renal Artery Stent Placement: Utility in Lesions Difficult to Treat with Balloon Angioplasty," Am. Coll. Cardiol., vol. 30, No. 6, pp. 1445-1450, Nov. 15, 1997. Abstract Only.

Williams, D.M. et al.; "Design and Testing of a High-FLo2 Autoperfusion Catheter: An Experimental Study," J. Vasc. Interv. Radiol., vol. 3, No. 2, pp. 285-290, May 1992. Abstract Only.

Zacherl, et al. Periarterial Papverine Applications Improves Intraoperative Kidney Function etc. Journal of Surgical Research 103:268-271 (2002).

* cited by examiner

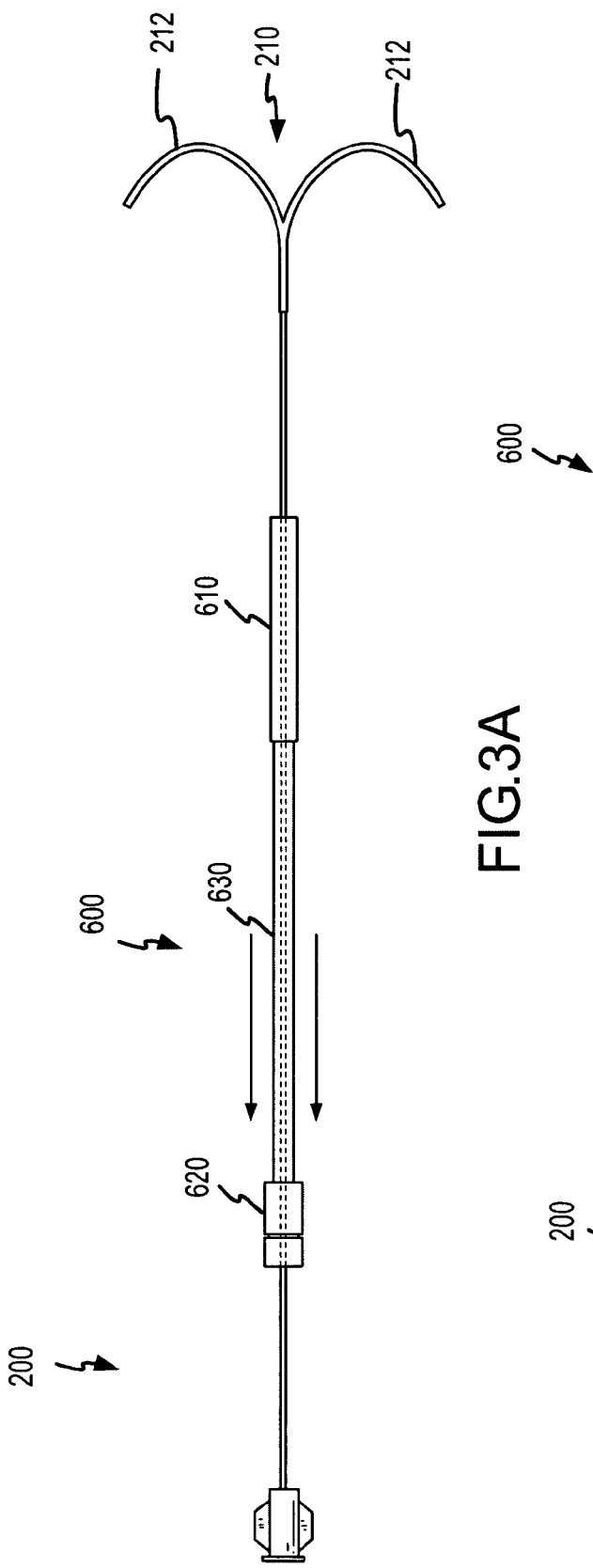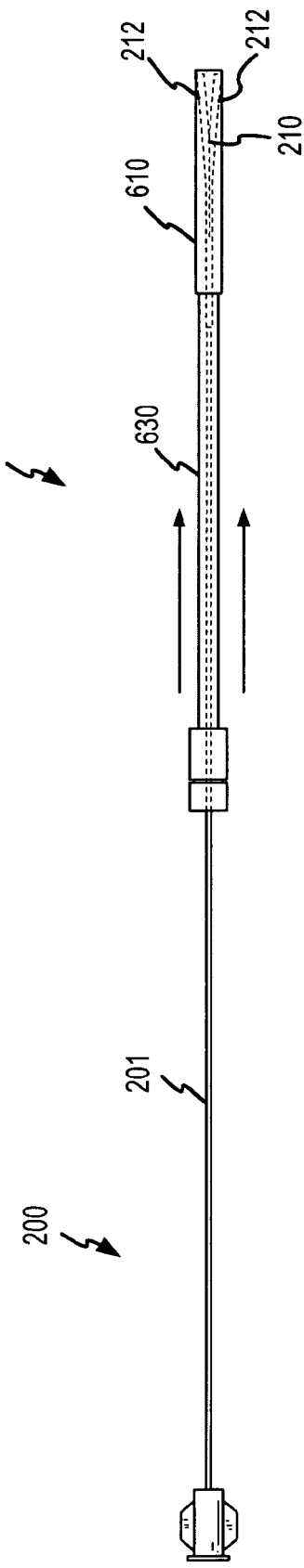

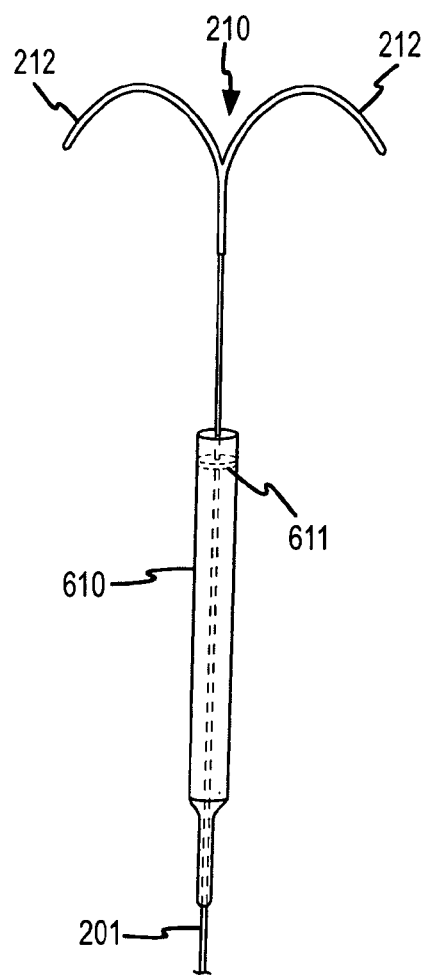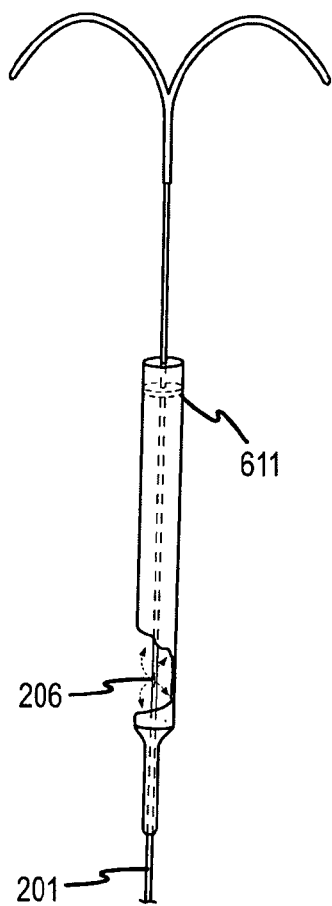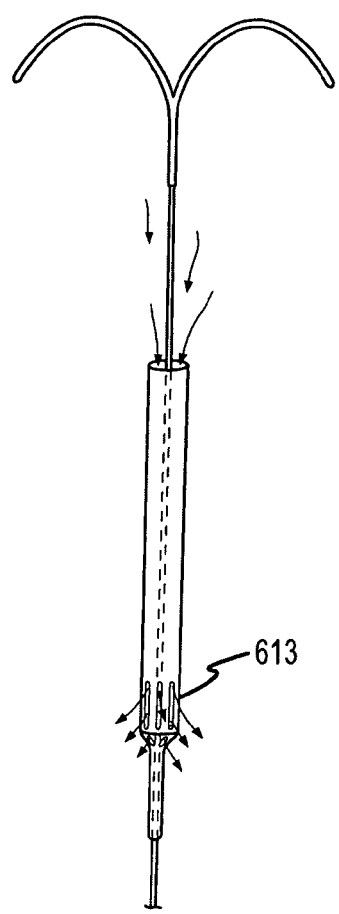
FIG.12A
FIG.12B
FIG.12C

RENAL INFUSION SYSTEMS AND METHODS

CROSS-REFERENCES TO RELATED APPLICATIONS

This application is a continuation-in-part of PCT Patent Application No. PCT/US2003/29740 filed Sep. 22, 2003, which claims the benefit of U.S. patent application Ser. No. 10/251,915 filed Sep. 20, 2002 now U.S. Pat. No. 7,063,679; and a continuation-in-part of PCT Patent Application No. PCT/US2004/008571 filed Mar. 19, 2004, which claims the benefit of U.S. Patent Application No. 60/508,751 filed Oct. 2, 2003; and a continuation-in-part of U.S. Patent application Ser. No. 11/084,738 filed Mar. 16, 2005 now U.S. Pat. No. 7,914,503, which is a continuation-in-part of PCT Patent Application No. PCT/US2003/29744 filed Sep. 22, 2003, which claims the benefit of U.S. Patent Application No. 60/476,347 filed Jun. 5, 2003 and of U.S. Patent Application No. 60/502,600 filed Sep. 13, 2003; and a continuation-in-part of U.S. patent application Ser. No. 11/084,434 filed Mar. 18, 2005 now U.S. Pat. No. 7,364,566, which is a continuation of PCT Patent Application No. PCT/US2003/29995 filed Sep. 22, 2003, which claims the benefit of U.S. Patent Application No. 60/412,343 filed Sep. 20, 2002, and of U.S. Patent Application No. 60/412,476 filed Sep. 20, 2002, and of U.S. Patent Application No. 60/479,329 filed Jun. 17, 2003, and of U.S. Patent Application No. 60/502,389 filed Sep. 13, 2003; and a continuation-in-part of U.S. patent application Ser. No. 11/083,802 filed Mar. 18, 2005, which is a continuation of PCT Patent Application No. PCT/US2003/29743 filed Sep. 22, 2003, which claims the benefit of U.S. Patent Application No. 60/486,349 filed Jul. 10, 2003; and a continuation-in-part of U.S. patent application Ser. No. 11/084,295 filed Mar. 18, 2005 now U.S. Pat. No. 6,994,700, which is a continuation of PCT Patent Application No. PCT/US2003/29585 filed Sep. 22, 2003, which claims the benefit of U.S. Patent Application No. 60/486,206 filed Jul. 9, 2003 and of U.S. Patent Application No. 60/502,399 filed Sep. 13, 2003; and a continuation-in-part of PCT Patent Application No. PCT/US2004/008573 filed Mar. 19, 2004, which claims the benefit of U.S. Patent Application No. 60/505,281 filed Sep. 22, 2003 and of U.S. Patent Application No. 60/543,671 filed Feb. 9, 2004; and a continuation-in-part of U.S. patent application Ser. No. 11/073,421 filed Mar. 4, 2005, which claims the benefit of U.S. Patent Application No. 60/550,632 filed Mar. 4, 2004 and of U.S. Patent Application No. 60/550,774 filed Mar. 5, 2004; and a continuation-in-part of U.S. patent application Ser. No. 11/129,101 filed May 13, 2005 now U.S. Pat. No. 7,585,836, which claims the benefit of U.S. Patent Application No. 60/571,057 filed May 14, 2004 and of U.S. Patent Application No. 60/612,731 filed Sep. 24, 2004; and claims the benefit of U.S. Provisional Patent Application No. 60/612,801 filed Sep. 24, 2004.

This application is also related to U.S. Pat. No. 6,749,598 filed Jan. 11, 1999, U.S. patent application Ser. No. 09/562,493 filed May 1, 2000 now U.S. Pat. No. 7,780,628, U.S. patent application Ser. No. 09/724,691 filed Nov. 28, 2000 now U.S. Pat. No. 7,122,019, PCT Patent Application No. PCT/US2003/29586 filed Sep. 22, 2003, U.S. Patent Application No. 60/582,870 filed Jun. 24, 2004, and U.S. patent application Ser. No. 11/167,056 filed Jun. 23, 2005. The entire contents of each of these applications and their priority filings is incorporated herein by reference for all purposes.

BACKGROUND OF THE INVENTION

This invention pertains generally to medical device systems and methods for delivering treatment to internal body lumens. More specifically, it is related to intra aortic renal treatment delivery systems and methods.

Many different medical device systems and methods have been previously described for locally delivering fluids or other agents into various body regions, including body lumens such as vessels, or other body spaces such as organs or heart chambers. Local fluid delivery systems may include drugs or other agents, or may even include locally delivering the body's own fluids, such as artificially enhanced blood transport, for example either entirely within the body such as directing or shunting blood from one place to another, or in extracorporeal modes such as via external blood pumps and the like. Local agent delivery systems are herein generally intended to relate to introduction of a foreign composition as an agent into the body, which may include drugs or other useful or active agents, and may be in a fluid form or other form such as gels, solids, powders, gases, and the like. It is to be understood that reference to only one of the terms fluid, drug, or agent with respect to local delivery descriptions may be made variously in this disclosure for illustrative purposes, but is not generally intended to be exclusive or omissive of the others; they are to be considered interchangeable where appropriate according to one of ordinary skill unless specifically described to be otherwise.

In general, local agent delivery systems and methods are often used for the benefit of achieving relatively high, localized concentrations of agent where injected within the body in order to maximize the intended effects there and while minimizing unintended peripheral effects of the agent elsewhere in the body. Where a particular dose of a locally delivered agent may be efficacious for an intended local effect, the same dose systemically delivered would be substantially diluted throughout the body before reaching the same location. The agent's intended local effect is equally diluted and efficacy is compromised. Thus systemic agent delivery requires higher dosing to achieve the required localized dose for efficacy, often resulting in compromised safety due to for example systemic reactions or side effects of the agent as it is delivered and processed elsewhere throughout the body other than at the intended target.

Various diagnostic systems and procedures have been developed using local delivery of dye (e.g. radiopaque contrast agent) or other diagnostic agents, wherein an external monitoring system is able to gather important physiological information based upon the diagnostic agent's movement or assimilation in the body at the location of delivery and/or at other locations affected by the delivery site. Angiography is one such practice using a hollow, tubular angiography catheter for locally injecting radiopaque dye into a blood chamber or vessel, such as for example coronary arteries in the case of coronary angiography, or in a ventricle in the case of cardiac ventriculography.

Other systems and methods have been reported for locally delivering therapeutic agent into a particular body tissue within a patient via a body lumen. For example, angiographic catheters of the type just described above, and other similar tubular delivery catheters, have also been reported for use in locally injecting treatment agents through their delivery lumens into such body spaces within the body. More detailed examples of this type include local delivery of thrombolitic drugs such as TPA™, heparin, cumadin, or urokinase into areas of existing clot or thrombogenic implants or vascular injury. In addition, various balloon catheter systems have also been reported for local administration of therapeutic agents into target body lumens or spaces, and in particular associated with blood vessels. More specific previously disclosed of this type include balloons with porous or perforated walls that elute drug agents through the balloon wall and into surrounding tissue such as blood vessel walls. Yet further examples for localized delivery of therapeutic agents include various multiple balloon catheters that have spaced balloons that are inflated to engage a lumen or vessel wall in order to isolate the intermediate catheter region from in-flow or out-flow across the balloons. According to these examples, a fluid agent delivery system is often coupled to this intermediate region in order to fill the region with agent such as drug that provides an intended effect at the isolated region between the balloons.

The diagnosis or treatment of many different types of medical conditions associated with various different systems, organs, and tissues, may also benefit from the ability to locally deliver fluids or agents in a controlled manner. In particular, various conditions related to the renal system would benefit a great deal from an ability to locally deliver of therapeutic, prophylactic, or diagnostic agents into the renal arteries.

Acute renal failure ("ARF") is an abrupt decrease in the kidney's ability to excrete waste from a patient's blood. This change in kidney function may be attributable to many causes. A traumatic event, such as hemorrhage, gastrointestinal fluid loss, or renal fluid loss without proper fluid replacement may cause the patient to go into ARF. Patients may also become vulnerable to ARF after receiving anesthesia, surgery, or a-adrenergic agonists because of related systemic or renal vasoconstriction. Additionally, systemic vasodilation caused by anaphylaxis, and anti-hypertensive drugs, sepsis or drug overdose may also cause ARF because the body's natural defense is to shut down, i.e., vasoconstrict, non-essential organs such as the kidneys. Reduced cardiac output caused by cardiogenic shock, congestive heart failure, pericardial tamponade, or massive pulmonary embolism creates an excess of fluid in the body, which can exacerbate congestive heart failure. For example, a reduction in blood flow and blood pressure in the kidneys due to reduced cardiac output can in turn result in the retention of excess fluid in the patient's body, leading, for example, to pulmonary and systemic edema.

Previously known methods of treating ARF, or of treating acute renal insufficiency associated with congestive heart failure ("CHF"), involve administering drugs. Examples of such drugs that have been used for this purpose include, without limitation: vasodilators, including for example papavarine, fenoldopam mesylate, calcium-channel blockers, neurohormonal modulators such as B-type natriuretic peptide (BNP) and atrial natriuretic peptide (ANP), acetylcholine, nifedipine, nitroglycerine, nitroprusside, adenosine, dopamine, and theophylline; antioxidants, such as for example acetylcysteine; and diuretics, such as for example mannitol, or furosemide. However, many of these drugs, when administered in systemic doses, have undesirable side effects. Additionally, many of these drugs would not be helpful in treating other causes of ARF. A septic shock patient with profound systemic vasodilation often has concomitant severe renal vasoconstriction, however administering vasodilators to dilate the renal artery to a patient suffering from systemic vasodilation would compound the vasodilation system wide. In addition, for patients with severe CHF (e.g., those awaiting heart transplant), mechanical methods, such as hemodialysis or left ventricular assist devices, may be implemented. Surgical device interventions, such as hemodialysis, however, generally have not been observed to be highly efficacious for long-term management of CHF. Such interventions would also not be appropriate for many patients with strong hearts suffering from ARF.

The renal system in many patients may also suffer from a particular fragility, or otherwise general exposure, to potentially harmful effects of other medical device interventions.

For example, the kidneys as one of the body's main blood filtering tools may suffer damage from exposed to high density radiopaque contrast dye, such as during coronary, cardiac, or neuro angiography procedures. One particularly harmful condition known as "radiocontrast nephropathy" or "RCN" is often observed during such procedures, wherein an acute impairment of renal function follows exposure to such radiographic contrast materials, typically resulting in a rise in serum creatinin levels of more than 25% above baseline, or an absolute rise of 0.5 mg/dl within 48-72 hours. Therefore, in addition to CHF, renal damage associated with RCN is also a frequently observed cause of ARF. In addition, the kidneys' function is directly related to cardiac output and related blood pressure into the renal system. These physiological parameters, as in the case of CHF, may also be significantly compromised during a surgical intervention such as an angioplasty, coronary artery bypass, valve repair or replacement, or other cardiac interventional procedure. Therefore, the various drugs used to treat patients experiencing ARF associated with other conditions such as CHF have also been used to treat patients afflicted with ARF as a result of RCN. Such drugs would also provide substantial benefit for treating or preventing ARF associated with acutely compromised hemodynamics to the renal system, such as during surgical interventions.

There would be great advantage therefore from an ability to locally deliver such drugs into the renal arteries, in particular when delivered contemporaneous with surgical interventions, and in particular contemporaneous with radiocontrast dye delivery. However, many such procedures are done with medical device systems, such as using guiding catheters or angiography catheters having outer dimensions typically ranging between about 4 French to about 12 French, and ranging generally between about 6 French to about 8 French in the case of guide catheter systems for delivering angioplasty or stent devices into the coronary or neurovascular arteries (e.g. carotid arteries). These devices also are most typically delivered to their respective locations for use (e.g. coronary ostia) via a percutaneous, transluminal access in the femoral arteries and retrograde delivery upstream along the aorta past the region of the renal artery ostia. A Seldinger access technique to the femoral artery involves relatively controlled dilation of a puncture hole to minimize the size of the intruding window through the artery wall, and is a preferred method where the profiles of such delivery systems are sufficiently small. Otherwise, for larger systems a "cut-down" technique is used involving a larger, surgically made access window through the artery wall.

Accordingly, an intra aortic renal agent delivery system for contemporaneous use with other retrogradedly delivered medical device systems, such as of the types just described above, would preferably be adapted to allow for such interventional device systems, in particular of the types and dimensions just described, to pass upstream across the renal artery ostia (a) while the agent is being delivered into the renal arteries, and (b) while allowing blood to flow downstream across the renal artery ostia, and (c) in an overall cooperating system that allows for Seldinger femoral artery access. Each one of these features (a), (b), or (c), or any sub-combination thereof, would provide significant value to patient treatment; an intra aortic renal delivery system providing for the combination of all three features is so much the more valuable.

Notwithstanding the clear needs for and benefits that would be gained from such intra aortic drug delivery into the renal system, the ability to do so presents unique challenges as follows.

In one regard, the renal arteries extend from respective ostia along the abdominal aorta that are significantly spaced apart from each other circumferentially around the relatively very large aorta. Often, these renal artery ostia are also spaced from each other longitudinally along the aorta with relative superior and inferior locations. This presents a unique challenge to deliver drugs or other agents into the renal system on the whole, which requires both kidneys to be fed through these separate respective arteries via their uniquely positioned and substantially spaced apart ostia. This becomes particularly important where both kidneys may be equally at risk, or are equally compromised, during an invasive upstream procedure—or, of course, for any other indication where both kidneys require renal drug delivery. Thus, an appropriate intra aortic delivery system for such indications would preferably be adapted to feed multiple renal arteries perfusing both kidneys.

In another regard, mere delivery of an agent into the natural, physiologic blood flow path of the aorta upstream of the kidneys may provide some beneficial, localized renal delivery versus other systemic delivery methods, but various undesirable results still arise. In particular, the high flow aorta immediately washes much of the delivered agent beyond the intended renal artery ostia. This reduces the amount of agent actually perfusing the renal arteries with reduced efficacy, and thus also produces unwanted loss of the agent into other organs and tissues in the systemic circulation (with highest concentrations directly flowing into downstream circulation).

In still a further regard, various known types of tubular local delivery catheters, such as angiographic catheters, other "end-hole" catheters, or otherwise, may be positioned with their distal agent perfusion ports located within the renal arteries themselves for delivering agents there, such as via a percutaneous transluminal procedure via the femoral arteries, or from other access points such as brachial arteries and the like. However, such a technique may also provide less than completely desirable results.

For example, such seating of the delivery catheter distal tip within a renal artery may be difficult to achieve from within the large diameter/high flow aorta, and may produce harmful intimal injury within the artery. Also, where multiple kidneys must be infused with agent, multiple renal arteries must be cannulated, either sequentially with a single delivery device, or simultaneously with multiple devices. This can become unnecessarily complicated and time consuming and further compound the risk of unwanted injury from the required catheter manipulation. Moreover, multiple dye injections may be required in order to locate the renal ostia for such catheter positioning, increasing the risks associated with contrast agents on kidney function (e.g. RCN)—the very organ system to be protected by the agent delivery system in the first place. Still further, the renal arteries themselves, possibly including their ostia, may have pre-existing conditions that either prevent the ability to provide the required catheter seating, or that increase the risks associated with such mechanical intrusion. For example, the artery wall may be diseased or stenotic, such as due to atherosclerotic plaque, clot, dissection, or other injury or condition. Finally, among other additional considerations, previous reports have yet to describe an efficacious and safe system and method for positioning these types of local agent delivery devices at the renal arteries through a common introducer or guide sheath shared with additional medical devices used for upstream interventions, such as angiography or guide catheters. In particular, to do so concurrently with multiple delivery catheters for simultaneous infusion of multiple renal arteries would further require a guide sheath of such significant dimensions that the preferred Seldinger vascular access technique would likely not be available, instead requiring the less desirable "cut-down" technique.

In addition to the various needs for delivering agents into branch arteries described above, much benefit may also be gained from simply enhancing blood perfusion into such branches, such as by increasing the blood pressure at their ostia. In particular, such enhancement would improve a number of medical conditions related to insufficient physiological perfusion into branch vessels, and in particular from an aorta and into its branch vessels such as the renal arteries.

Certain previous reports have provided surgical device assemblies and methods intended to enhance blood delivery into branch arteries extending from an aorta. For example, intra-aortic balloon pumps (IABPs) have been disclosed for use in diverting blood flow into certain branch arteries. One such technique involves placing an IABP in the abdominal aorta so that the balloon is situated slightly below (proximal to) the branch arteries. The balloon is selectively inflated and deflated in a counterpulsation mode (by reference to the physiologic pressure cycle) so that increased pressure distal to the balloon directs a greater portion of blood flow into principally the branch arteries in the region of their ostia. However, the flow to lower extremities downstream from such balloon system can be severely occluded during portions of this counterpulsing cycle. Moreover, such previously reported systems generally lack the ability to deliver drug or agent to the branch arteries while allowing continuous and substantial downstream perfusion sufficient to prevent unwanted ischemia.

It is further noted that, despite the renal risks described in relation to radiocontrast dye delivery, and in particular RCN, in certain circumstances delivery of such dye or other diagnostic agents is indicated specifically for diagnosing the renal arteries themselves. For example, diagnosis and treatment of renal stenosis, such as due to atherosclerosis or dissection, may require dye injection into a subject renal artery. In such circumstances, enhancing the localization of the dye into the renal arteries may also be desirable. In one regard, without such localization larger volumes of dye may be required, and the dye lost into the downstream aortic flow may still be additive to impacting the kidney(s) as it circulates back there through the system. In another regard, an ability to locally deliver such dye into the renal artery from within the artery itself, such as by seating an angiography catheter there, may also be hindered by the same stenotic condition requiring the dye injection in the first place (as introduced above). Still further, patients may have stent-grafts that may prevent delivery catheter seating.

Notwithstanding the interest and advances toward delivering agents for treatment or diagnosis of organs or tissues, the previously reported systems and methods summarized immediately above often lack the ability to effectively deliver agents from within a main artery and locally into substantially only branch arteries extending therefrom while allowing the passage of substantial blood flow and/or other medical devices through the main artery past the branches. This is in particular the case with previously reported renal treatment and diagnostic devices and methods, which do not adequately provide for local delivery of agents into the renal system from a location within the aorta while allowing substantial blood flow continuously downstream past the renal ostia and/or while allowing distal medical device assemblies to be passed retrogradedly across the renal ostia for upstream use. Much benefit would be gained if agents, such as protective or therapeutic drugs or radiopaque contrast dye, could be delivered to one or both of the renal arteries in such a manner.

Several more recently reported advances have included local flow assemblies using tubular members of varied diameters that divide flow within an aorta adjacent to renal artery ostia into outer and inner flow paths substantially perfusing the renal artery ostia and downstream circulation, respectively. Such reports further include delivering fluid agent primarily into the outer flow path for substantially localized delivery into the renal artery ostia. These reported systems and methods represent exciting new developments toward localized diagnosis and treatment of pre-existing conditions associated with branch vessels from main vessels in general, and with respect to renal arteries extending from abdominal aortas in particular.

However, such previously reported designs would still benefit from further modifications and improvements in order to: maximize mixing of a fluid agent within the entire circumference of the exterior flow path surrounding the tubular flow divider and perfusing multiple renal artery ostia; use the systems and methods for prophylaxis and protection of the renal system from harm, in particular during upstream interventional procedures; maximize the range of useful sizing for specific devices to accommodate a wide range of anatomic dimensions between patients; and optimize the construction, design, and inter-cooperation between system components for efficient, atraumatic use.

A need still exists for improved devices and methods that allow the physician to leave an introducer sheath in place while advancing and retracting a jacket sheath. Similarly, a need still exists for improved devices and methods that provide a short introducer sheath that allows for a one-size-fits-all approach for placing a delivery catheter in the patient's body. Relatedly, the need still exists for improved approaches that do not require an introducer sheath that is optimally sized in each case according to the patient's anatomy (e.g. the distance from the puncture site to the renal artery origins or ostia). What is more, the need still exists for improved devices and methods that avoid the need to have excess external sheath length extending proximally from the entry site, as may be the case where the distance between the puncture site and the deployment site is significantly less the length of a standard introducer sheath. Further, a need still exists for improved devices and methods that create less interference or friction when the physician maneuvers various components of the catheter device 10. A need still exists for improved approaches that avoid or minimize the risk of having an inadequate length for an auxiliary catheter such as a coronary catheter to reach its intended site.

A need still exists for improved devices and methods that can eliminate many of the difficulties associated with managing iliac, aortic, and other vascular tortuosity. Further, a need still exists for improved approaches that minimize the potential for clot formation within treatment delivery systems. Relatedly, a need still exists for improved approaches that decrease the risk of clots dislodging when adjunctive commercial products are passed through the introducer sheath, particularly at advancement. And the need still exists for improved approaches that provide a full-covered advancement of bifurcated catheter to the intended deployment site. Further, the need still exists for improved devices and methods that facilitate adjunctive coronary procedures, as well as various peripheral procedures. The present invention provides solutions for at least some of such needs.

BRIEF SUMMARY OF THE INVENTION

The present invention provides a treatment delivery system that is easy to use and minimizes the time required for many surgical procedures. With the incorporation of an improved introducer sheath, an integrated introducer and catheter system can provide universal application for a broad spectrum of patients, for various types of catheterization protocols, regardless of the unique anatomical features of the individual patient. Moreover, a moveable cover jacket sheath or other constraining assembly or structure allows for advancement and retraction of distal catheter tips or extensions in a collapsed or captured state. Constraining assemblies may include jackets, sheaths, loops, lassos, rings, and the like. The present invention also provides for improved guide wire guidance and advancement of the cover jacket sheath and catheter assembly for advancement. Guide wire systems can be of a coaxial design (e.g wire inside cover jacket sheath) or of a monorail type design, including a split-tube type of monorail to allow the rail to snap onto and off of the catheter shaft. Further, the present invention provides several improved cover jacket sheath configurations, which can allow blood passage therethrough, to avoid stagnant blood and potential thrombus formation within the jacket sheath. Many jacket sheath configurations may be sealed during the dwell period, including those which allow infusate to fill the sealed inner jacket space volume to prevent thrombus formation. It is further appreciated that the present invention provides a highly integrated catheter and sheath system where many components, including the constraining jacket sheath, remain together without extraneous tubes, wires, and the like protruding outside the introducer assembly's Y-hub during the dwell period.

These present embodiments therefore are particularly useful in intra aortic renal drug delivery systems introduces from a position proximal to the renal arteries; however, it is contemplated that these systems and methods may be suitably modified for use in other anatomical regions and for other medical conditions without departing from the broad scope of various of the aspects illustrated by the embodiments. For example, intra aortic fluid delivery according to various of these embodiments benefits from particular dimensions, shapes, and constructions for the subject devices herein described. However, suitable modifications may be made to deliver fluids to other multi-lateral branch structures from main body spaces or lumens such as other locations within the vasculature, including the right and left coronary artery ostia, fallopian tubes stemming from a uterus, or the gastrointestinal tract.

In a first aspect, the present invention provides a method for positioning a delivery catheter in the renal arteries. The method can include positioning an introducer sheath in an iliac artery, advancing a renal delivery catheter having a distal bifurcation through the introducer sheath, constraining the distal bifurcation in a low-profile configuration, advancing the constrained distal bifurcation from the introducer sheath toward the renal arteries while the bifurcation remains constrained, and releasing the distal bifurcation from the constrained low-profile configuration to allow entry of a first distal extension of the distal bifurcation into one of the renal arteries and a second distal extension of the distal bifurcation into the other renal artery. In some aspects, constraining the distal bifurcation in the low-profile configuration includes constraining the distal bifurcation with a sheath, a ring capture system, or a guide wire ring. In some aspects, passing the constrained distal bifurcation from the introducer sheath toward the renal arteries includes advancing the sheath over a guide wire, advancing the ring capture system along a guide wire, or advancing a guide wire ring along a guide wire. In a related aspect, the method can also include advancing a second catheter through the introducer sheath, and performing a diagnostic or interventional procedure with the second catheter.

In another aspect, the present invention provides a system for delivering treatment to the renal arteries. The system can include a delivery catheter having a distal bifurcation, and an introducer assembly having an introducer sheath in operative association with a Y-hub. The introducer sheath can have a length in the range from about 5 cm to about 25 cm. The Y-hub can have a first port for receiving the delivery catheter and a second port for receiving a second catheter. The system can also include a constraint assembly for holding the distal bifurcation of the delivery catheter in a low-profile configuration when it is advanced distally beyond the introducer sheath. In some aspects, the constraint assembly may include a jacket sheath for holding the distal bifurcation of the delivery catheter in a low-profile configuration when it is advanced distally beyond the introducer sheath. The jacket sheath can include a guide for receiving a guide wire. The jacket sheath can also include a split tube. In some cases, the jacket sheath includes distal and proximal flow apertures. In some cases, the jacket sheath can be in sealed cooperation with the delivery catheter. Relatedly, the delivery catheter can include a delivery catheter port for delivering an infusate to an interior of the jacket sheath. In some cases, the constraint assembly can include a collapsible ring capture system or a guide wire ring.

In another aspect, the present invention provides a method of positioning a delivery catheter in a branch lumen extending from a main lumen in a body of a patient. The method can include positioning an introducer sheath in the main lumen, advancing a delivery catheter having a distal bifurcation through the introducer sheath, constraining the distal bifurcation in a low-profile configuration, advancing the constrained distal bifurcation from the introducer sheath toward the branch lumen, and releasing the distal bifurcation from the constrained low-profile configuration to allow entry of a first distal extension of the distal bifurcation into the branch lumen. In some cases, advancing the introducer sheath in the main lumen can include advancing the introducer sheath through a puncture in a first femoral artery of the patient. The method can also include advancing a guide catheter through the introducer sheath toward a second femoral artery of the patient via the aortic bifurcation. In some cases, constraining the distal bifurcation in the low-profile configuration can include constraining the distal bifurcation with a sheath, a ring capture system, or a guide wire ring.

For a fuller understanding of the nature and advantages of the present invention, reference should be had to the ensuing detailed description taken in conjunction with the accompanying drawings.

BRIEF DESCRIPTION OF THE DRAWINGS

FIG. 3A illustrates a delivery catheter and constraint assembly according to one embodiment of the present invention.

FIG. 3B illustrates a delivery catheter and constraint assembly according to one embodiment of the present invention.

FIG. 12A illustrates a delivery catheter and constraint assembly according to one embodiment of the present invention.

FIG. 12B illustrates a delivery catheter and constraint assembly according to one embodiment of the present invention.

FIG. 12C illustrates a delivery catheter and constraint assembly according to one embodiment of the present invention.

DETAILED DESCRIPTION OF THE INVENTION

Figure 1:
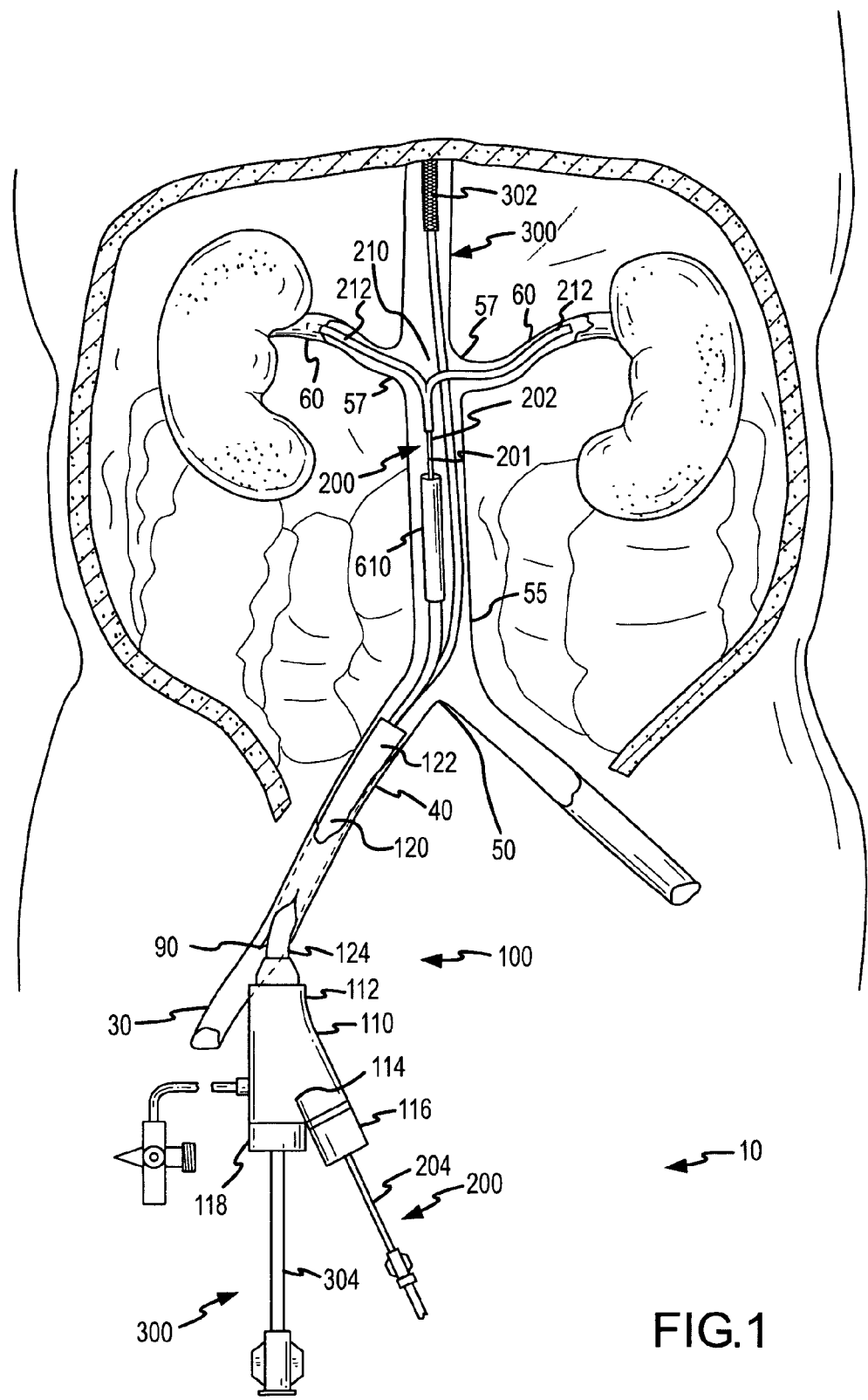
FIG. 1 illustrates a renal delivery system according to one embodiment of the present invention.

As discussed herein the present invention can be provided to the physician as an integrated catheter-sheath system, and can eliminate the operational step of determining the proper sheath sizing to use for a particular patient. Alternatively, the various components of the system may be provided independently or in different combinations with each other or with other conventional catheter system components. The present invention is well suited for both coronary and contralateral procedures.

The description herein provided relates to medical material delivery systems and methods in the context of their relationship in use within a patient's anatomy. Accordingly, for the purpose of providing a clear understanding, the term proximal should be understood to mean locations on a system or device relatively closer to the operator during use, and the term distal should be understood to mean locations relatively further away from the operator during use of a system or device. These present embodiments below therefore generally relate to local renal drug delivery generally from the aorta; however, it is contemplated that these systems and methods may be suitably modified for use in other anatomical regions and for other medical conditions without departing from the broad scope of various of the aspects illustrated by the embodiments.

In general, the disclosed material delivery systems will include a fluid delivery assembly, a proximal coupler assembly and one or more elongated bodies, such as tubes or catheters. These elongated bodies may contain one or more lumens and generally consist of a proximal region, a mid-distal region, and a distal tip region. The distal tip region will typically have means for delivering a material such as a fluid agent. It is appreciated, however, that the present systems may be configured to deliver any of a wide variety of treatment modalities, including the therapeutic application of ultrasound and other types of treatment energy. Radiopaque markers or other devices may be coupled to the specific regions of the elongated body to assist introduction and positioning.

The material delivery system is intended to be placed into position by a physician, typically either an interventionalist (e.g. a cardiologist or radiologist) or an intensivist, a physician who specializes in the treatment of intensive-care patients. The physician will gain access to a femoral artery in the patient's groin, typically using a Seldinger technique of percutaneous vessel access or other conventional method.

For additional understanding, further more detailed examples of other systems and methods for providing local renal drug delivery are variously disclosed in the following published references: WO 00/41612 to Keren et al.; and WO 01/83016 to Keren et al. The disclosures of these references are herein incorporated in their entirety by reference thereto. Moreover, various combinations with, or modifications according to, various aspects of the present embodiments as would be apparent to one of ordinary skill upon review of this disclosure together with these references are also considered within the scope of invention as described by the various independently beneficial embodiments described below.

Turning now to the drawings, FIG. 1 illustrates a renal delivery system 10 according to one embodiment of the present invention. System 10 includes an introducer assembly 100, a renal delivery catheter 200, and a coronary guide catheter 300 suitably for introducing, for example, a balloon angioplasty catheter (not shown). Introducer assembly 100 can have a Y-hub 110 and an introducer sheath 120. Typically, Y-hub distal end 112 is coupled with introducer sheath proximal end 124. Delivery catheter 200 includes a delivery catheter shaft 201 having a distal end 202 and a proximal end 204. Renal delivery catheter shaft 201 is partially disposed within introducer assembly 100, such that delivery catheter shaft distal end 202 extends from introducer sheath distal end 122, and delivery catheter shaft proximal end 204 extends from a first port 116 of Y-hub proximal end 114. Similarly, coronary guide catheter 300 is partially disposed within introducer assembly 100, such that coronary guide catheter distal end 302 extends from introducer sheath distal end 122, and coronary guide catheter proximal end 304 extends from a second port 118 of Y-hub proximal end 114. Introducer sheath 120 can have a length selected to terminate well below the renal arteries, preferably below the aortic branch 50. The length is typically in the range from about 5 cm to about 25 cm, typically from about 10 cm to about 15 cm. In many cases, introducer sheath 120 will have a very thin wall. The wall may be as thin as possible or practical, which can allow for an optimal vessel entry profile and a greater inner diameter. In some cases, the outer diameter of introducer sheath 120 may be, for example, less than or equal to 1 French greater than its inner diameter. In other cases, the outer diameter may be about 2 French greater than the inner diameter. In related cases, the difference between the outer diameter of introducer sheath and its inner diameter may be within the range of between about 0.005" to about 0.0025", or within the range of between about 0.009" to about 0.015".

Introducer assembly 100 allows for the placement of renal delivery catheter 200 and coronary guide catheter 300 (as well as associated interventional catheters) into a patient's vasculature via a single vessel entry puncture 90. In some cases, system 10 can be used for renal drug infusion during a primary catheterization procedure, such as a coronary intervention. Advantageously, introducer sheath 120 can simultaneously facilitate introduction of infusion catheter 200 for a renal infusion procedure, and introduction of coronary guide catheter 300 for a coronary procedure. Typically, introducer sheath 120 is advanced through single puncture 90 in a femoral artery 30 or an iliac artery 40 of the patient, below or caudal to the aortic bifurcation 50. Delivery catheter 200 and coronary guide catheter 300 are then inserted through introducer assembly 100, into the patients' body, to their respective desired locations. FIG. 1 illustrates delivery catheter 200 having a distal bifurcation 210 in a deployed high-profile configuration. As further discussed below, system 10 can include a jacket sheath 610 for constraining a distal bifurcation 210 of delivery catheter 200 in a low-profile position.

The present inventors have discovered that an introducer sheath 120 having the above-described dimensions can provide the physician with many practical operational advantages. For example, the physician can leave introducer sheath 120 in place while retracting and advancing jacket sheath 610, thereby simplifying the cannulation procedure. Moreover, a short introducer sheath 120 allows for a one-size-fits-all approach for placing delivery catheter 200 in the patient's body, as the system does not require an introducer sheath that is optimally sized in each case according to the patient's anatomy (e.g. the distance from the puncture site to the renal artery origins or ostia). Such features are highly amenable to improved standardization in case planning. Universal sizing can eliminate the need to use introducer sheaths that are pre-sized to fit the patient's anatomy.

Relatedly, the present invention avoids the need to have excess external sheath length extending proximally from the entry site, as may be the case where the distance between the puncture site and the deployment site is significantly less the length of standard introducer sheaths. And where it is necessary to retract introducer sheath 120 from the patient, the reduced length extending proximally from the patient will create less interference where the physician may need to maneuver other components of device 10. By reducing the length of introducer sheath 120 that extends proximally from the patient, it is possible to avoid or minimize the risk of having an inadequate length for an auxiliary catheter such as a coronary catheter to reach its intended site. In other words, a shortened introducer sheath 120 can allow Y-hub 110 to be disposed closer to a vessel entry point such as puncture 90. In general, coronary guide catheters are sized to span the typical distance from a vessel entry site to the coronary arteries. Using a shortened introducer sheath 120 avoids the situation where a guide catheter is coupled with introducer assembly 100 but remains too far from the groin entry, such that during the procedure the proximal end of the guide catheter engages Y-hub 110 before the distal end of the guide catheter reaches the target coronary vessel. Auxiliary components of device 10 will therefore encounter less interference or friction from introducer sheath 120 within the interior of the patient's vessel. Advantageously, use of the present invention eliminates many of the difficulties associated with managing iliac, aortic, and other vascular tortuosity.

Standard length introducer sheaths are often placed directly in the aorta, and catheter devices are continuously passed therethrough. In some cases, a longer length sheath can increases the propensity to clot as there may be more stagnant area. Relatedly, a sheath end in the aorta is typically exposed to higher flow than a sheath end in the iliac or femoral artery, as there is a higher likelihood that blood will enter the sheath end and thus possibly clot. Advantageously, the shortened introducer sheath dimensions of the present invention may minimize the potential for clot formation within introducer sheath 120 and Y-hub 110 by removing the sheath end from the aortic flow. Thus, the present systems can in some cases eliminate or reduce the need for a constant saline or heparinized saline drip, which is intended to prevent clotting in introducer sheath 120. Relatedly, in some cases there can be an increased risk of clots dislodging when adjunctive commercial products are passed through standard length introducer sheaths, particularly at advancement. The introducer sheath 120 of the present invention can minimize such risks. The present invention confers such benefits while still providing a full-covered advancement of distal bifurcation 210 to the intended deployment site. Accordingly, the present invention provides a system with improved stability characteristics.

The length of introducer sheath 120 can be such that delivery catheter 200 and coronary catheter 300 can both exit introducer sheath 120 well below the renal arteries. Thus, there is less opportunity to displace delivery catheter 200 when advancing coronary catheter 300. Similarly, because a distal bifurcation 210 of delivery catheter 200 is typically not maintained within introducer sheath 120, it is unlikely that significant friction or other jamming complications will develop between coronary guide catheter 300 and delivery catheter 200. This is true whether delivery catheter distal end 210 is in a deployed or undeployed configuration. In other words, the length of introducer sheath 120 can allow adjunctive coronary catheter 300 to exit introducer sheath 120 at a sufficient distance from renal arteries 60, so as to provide improved stability of delivery catheter 200 as it interacts with renal arteries 60. Because the length of introducer sheath 120 reduces the need to manage vessel tortuosity and possible interference with other system components, the need for substantial columnar and radial support for sheath 120, for example from coil reinforcements, can be eliminated or greatly reduced. Introducer sheath 120 can be prepared with a thin wall extrusion, where the thickness of the wall is less than currently used multi-layer and reinforced sheath tubes.

In addition to facilitating various coronary procedures, the present invention can also be used in conjunction with a wide variety of peripheral procedures. In one example, the present invention can be used in contralateral superficial femoral artery (SFA) vessel advancement for critical limb salvage cases, which may be particularly useful in treating diabetic patients. Similarly, the present invention can be used to effect various procedures in the abdominal or femoral arteries, and can be used to treat occlusive peripheral vascular disease, critical limb ischemia, and other related conditions.

Figure 2:
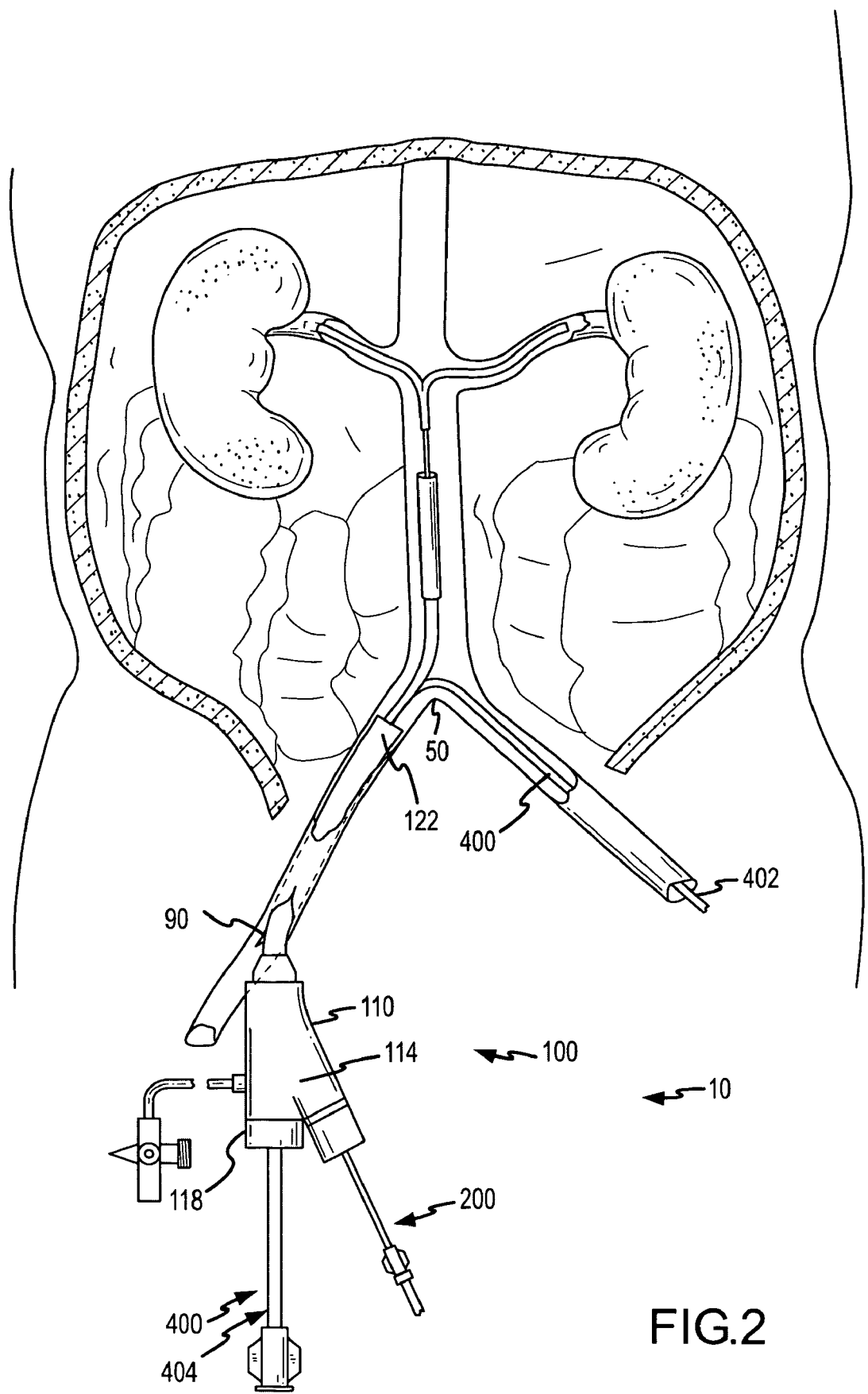
FIG. 2 illustrates a renal delivery system according to one embodiment of the present invention.

FIG. 2 illustrates a renal delivery system 10 according to one embodiment of the present invention which is well suited for such peripheral procedures. Toward this end, system 10 can include an introducer assembly 100, a delivery catheter 200, and a peripheral guide catheter 400. Peripheral guide catheter 400 is partially disposed within introducer assembly 100, such that peripheral guide catheter distal end 402 extends from introducer sheath distal end 122, and peripheral guide catheter proximal end 404 extends from a second port 118 of Y-hub proximal end 114. A renal infusion may be performed simultaneously with a contralateral iliac vessel procedure via a single vessel entry 90 through introducer assembly 100. Because introducer sheath distal end 122 can sit below the aortic bifurcation 50, system 10 can be used in "up-and-over" procedures where contralateral access is desired. Consequently, there is no need to retract introducer sheath 120 to situate its distal end below the aortic bifurcation 50, and similarly, there is no need to perform additional manipulations of peripheral catheter 400 at Y-hub 110 which could otherwise be far from the vessel entry site if a standard length introducer sheath were used. Introducer sheath 120 provides optimal use of the working length of peripheral catheter 400, which will often be helpful for extremely distal procedures, and provides optimal handling characteristics to peripheral catheter 400. Thus, the present invention provides a system that can be universally used for femoral-based coronary procedures and peripheral procedures alike. Present system 10 can reduce friction on peripheral catheter 400, as the length of introducer sheath 120, through which both delivery catheter 200 and peripheral catheter 400 pass, is minimized.

In some embodiments, delivery catheter 200 can be used to deliver a therapeutic or diagnostic infusate to the renal arteries. It is also appreciated that delivery catheter 200 can be used to effect a wide variety of other therapeutic and diagnostic modalities at or near the renal ostia 57 or renal arteries 60, including stent placement, therapeutic energy delivery, and the like.

The present invention also provides means for maintaining distal bifurcation 210 of delivery catheter 200 in a constrained or otherwise undeployed or protected configuration. FIGS. 3A and 3B illustrate a constraint assembly 600 according to one embodiment of the present invention. Constraint assembly 600 includes a jacket sheath 610 coupled with a lead 630, which may in turn be coupled with a connector 620. FIG. 3A depicts delivery catheter 200 in an unconstrained or deployed configuration. Jacket sheath 610 is retracted from delivery catheter distal bifurcation 210. Delivery catheter 200 may be introduced via a sacrificial long thin-wall covering jacket 610, which can be removed after deployment. In such cases, delivery catheter 200 can be retracted without being constrained by jacket sheath 610. As shown in FIG. 3B, by advancing lead 630 in a distal direction along delivery catheter shaft 201, jacket sheath 610 envelops and forces distal bifurcation 210 into a collapsed, undeployed, low profile configuration. In this way, lead 630 can be retracted or advanced along the length of delivery catheter shaft 201 so as to deploy or undeploy distal bifurcation 210. In some cases, distal jacket sheath 610 may also be referred to as a movable cover jacket or capture sheath. Often, the diameter of jacket sheath 610 will be only as large as necessary to contain distal extensions or tips 212 of delivery catheter 200.

Typically, delivery catheter distal end 210 is in the undeployed configuration when it is inserted into the patient's body via introducer assembly 100. With supplemental reference to FIG. 1, for example, the physician may advance the constrained delivery catheter distal end 210 through the patient's femoral artery 30, through the iliac artery 40, past the aortic branch 50, and through the aorta 55 to the desired deployment location at or near the renal ostia 57. The physician can then manipulate constraint assembly 600 so as to deploy distal bifurcation 210, thereby initiating a renal cannulation procedure. Often, distal bifurcation 210 includes distal extensions 212, and deployment involves engaging distal extensions 212 with renal arteries 60. By advancing an undeployed delivery catheter distal bifurcation 210 into the patient's body, it is possible to avoid causing vessel trauma with distal extensions 212. It is believed that in many cases, it may be difficult to advance delivery catheter distal bifurcation 210 in the deployed configuration. The collapsed and low-profile state facilitates advancement of the distal end distal extensions 212 through the patient's vasculature. In some cases, as soon as distal end 210 is allowed to change from a constrained to an unconstrained configuration, distal extensions 212 are automatically cannulated In other instances, distal extensions 212 are cannulated some time after distal bifurcation 210 is changed from the constrained configuration to the unconstrained configuration.

Constraint assembly 600 may be designed and used in a number of ways. For example, as seen in FIG. 3A, lead 630 can include a thin-wall outer membrane that sheathes delivery catheter shaft 201. In this embodiment, lead 630 is intended to remain intact, as a movable outer member over shaft 201 in a coaxial fashion. By advancing or retracting outer member lead 630, cover jacket 610 captures or releases distal extensions 212 of distal bifurcation 210. In this sense, the deployed configuration refers to the open or high-profile configuration. Incorporation of outer member lead 630 can add functional outer diameter to delivery catheter shaft 201, and may in some cases require a smaller catheter shaft 201 if the outer diameter of lead 630 is equal to or smaller than the original diameter of shaft 201. Relatedly, incorporation of outer member 630 may require an upsizing in the functional diameter of the catheter shaft 201.

It is appreciated that the present invention contemplates a wide variety of means for reversibly covering or restraining distal extensions 212 in their collapsed state. As further discussed below, constraint assemblies can include various combinations of jackets, sheaths, sleeves, covers, control wires or rods, and the like. It is further appreciated the present invention may include or otherwise be in operative association with guidance assemblies such as guide wires so as to ensure desired placement of device 10 in the patient's body. Guide wire guidance can allow guided advancement of delivery catheter 200 and/or guide catheter 300, 400 during deployment, cannulation, and removal. In some cases, guide wire guidance may not be required for device removal. For example, device removal may simply involve retracting distal extensions 212 into jacket 610, and atraumatically withdrawing collapsed bifurcated end 210 through the vasculature and out of introducer sheath 120 and entry site.

Figure 4:
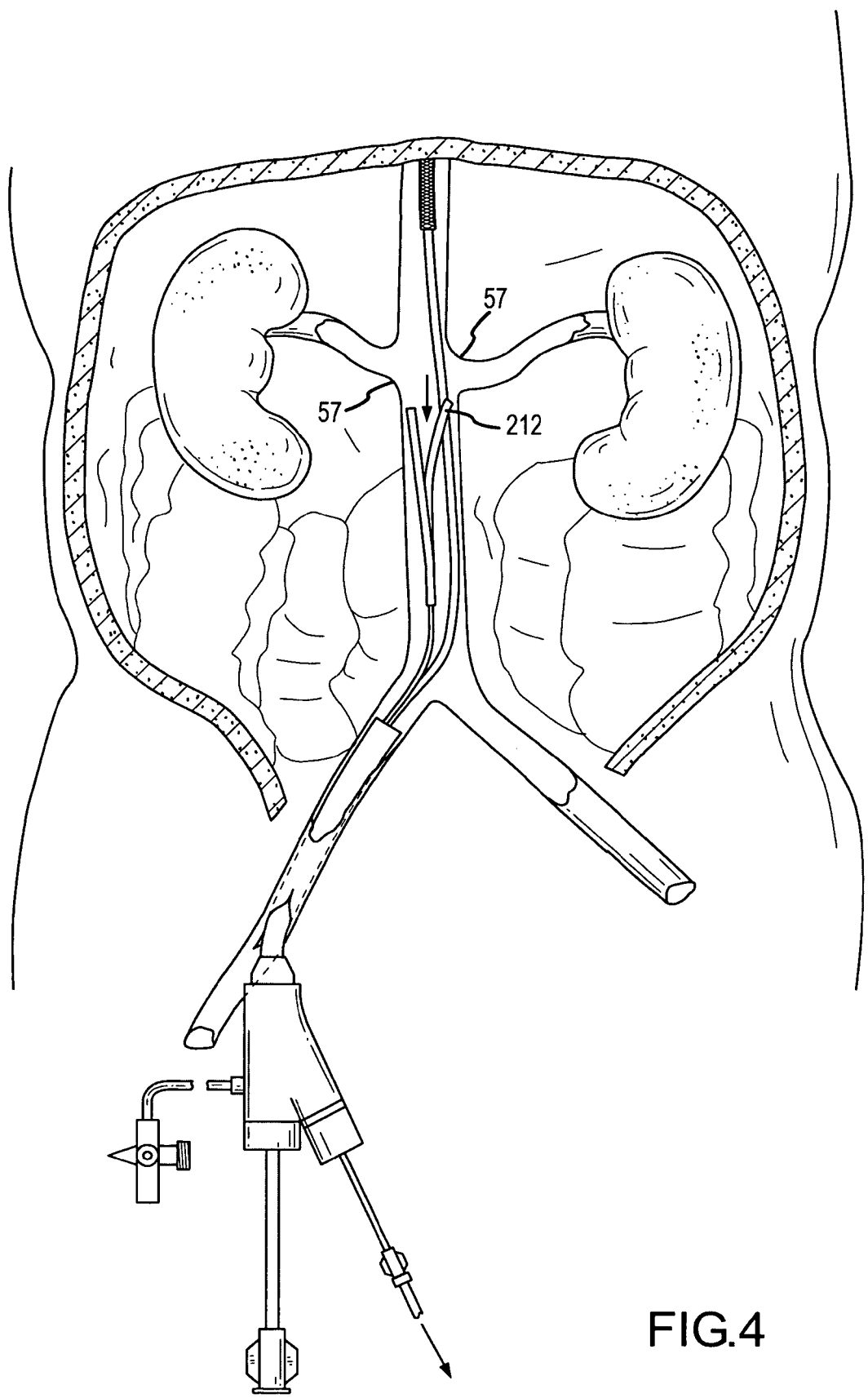
FIG. 4 illustrates a renal delivery system according to one embodiment of the present invention.

Device 10 may be retracted in either the collapsed or uncollapsed configuration. In some cases, distal extensions 212 are sufficiently soft and pliable to be retracted in an uncollapsed configuration from the patient's renal ostia 57 without causing damage, as shown in FIG. 4. For example, in some percutaneous applications, it is often sufficient to remove delivery catheter 200 while distal extensions 212 are still in the uncollapsed configuration. In other cases, a physician will remove device 10 in the collapsed atraumatic configuration to reduce the potential of vessel trauma and displacement of plaques, thrombi, and the like.

Figure 5A:
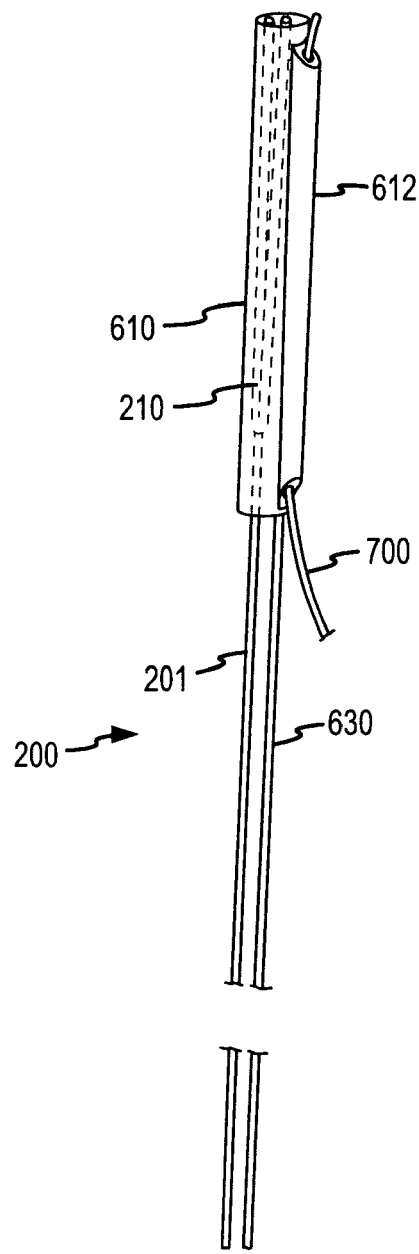
FIG. 5A illustrates a delivery catheter and constraint assembly according to one embodiment of the present invention.
Figure 5B:
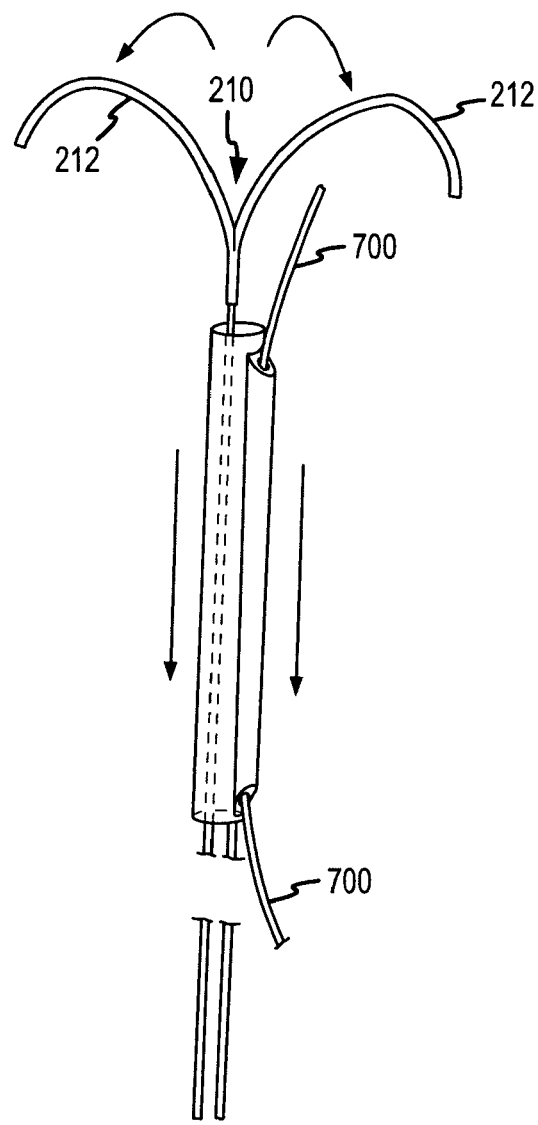
FIG. 5B illustrates a delivery catheter and constraint assembly according to one embodiment of the present invention.

FIGS. 5A and 5B illustrate a particular embodiment of the present invention that uses a monorail guidance system. Delivery catheter 200 shown in FIG. 5A is undeployed, as jacket sheath 610 of constraint assembly 600 maintains distal bifurcation 210 in a low profile configuration. Jacket sheath 610 includes a guide 612 adapted to slidably receive a guide wire 700. Here, guide 612 includes a longitudinal tube affixed with the body of sheath 610, in such a way that guide wire 700 is disposed laterally to the internal lumen of sheath 610. It is appreciated that in other embodiments, guide 612 may include other means for slidably engaging guide wire 700. When delivery catheter 200 is advanced through the patient's artery, guide 612 slides along guide wire 700, while at the same time remaining fixed relative to delivery catheter distal bifurcation 210. In one embodiment, lead 630 includes a control wire or rod instead of an axially disposed cylindrical outer member, and thus is not of a full coaxial design over the delivery catheter shaft 201. Cover jacket 610 may be coaxially located on delivery catheter shaft 201, which remains permanently over delivery catheter shaft 201. Delivery catheter 200 shown in FIG. 5B is in a deployed configuration, as jacket sheath 610 is retracted away from distal bifurcation 210. Typically, this retraction also involves sliding guide 612 in a proximal direction along guide wire 700, although in some embodiments retraction of constraint assembly 600 will be accompanied by retraction of guide wire 700. In some cases, guide 612 may include a series of segmented tubular segments. In related cases, guide 612 may include a partially tubular segment having a C-shaped cross section, whereby guide 612 may be snapped onto and off of guide wire 700.

As discussed above, jacket sheath 610 may be coupled with lead 630 for advancement and retraction. It is appreciated that lead 630 can include any of a variety of control wires, or small diameter shafts or rods. In some iterations, lead 630 is permanently attached with jacket sheath 610, and in others it is removably coupled with jacket sheath 610. In some cases, jacket sheath 610 can be positioned just outside of introducer assembly Y-hub 110 without an attached lead 630. This configuration is facilitated by the option of the ability to remove or detach lead 630 from jacket sheath 610. On the other hand, the option of having lead 630 permanently connected with cover jacket sheath 610 can provide simplicity in manufacture as well as potentially high strength and ease of use. In some embodiments, lead 630 is approximately 35 cm in length, and sufficiently narrow in diameter so as not to interfere with the catheterization procedure. Another design for the detachable lead 630 uses a means of connection of the cover jacket to currently available wires such as a guide wire, and one is meant for a dedicated control wire, with specific means of connection to the jacket.

Figure 6A:
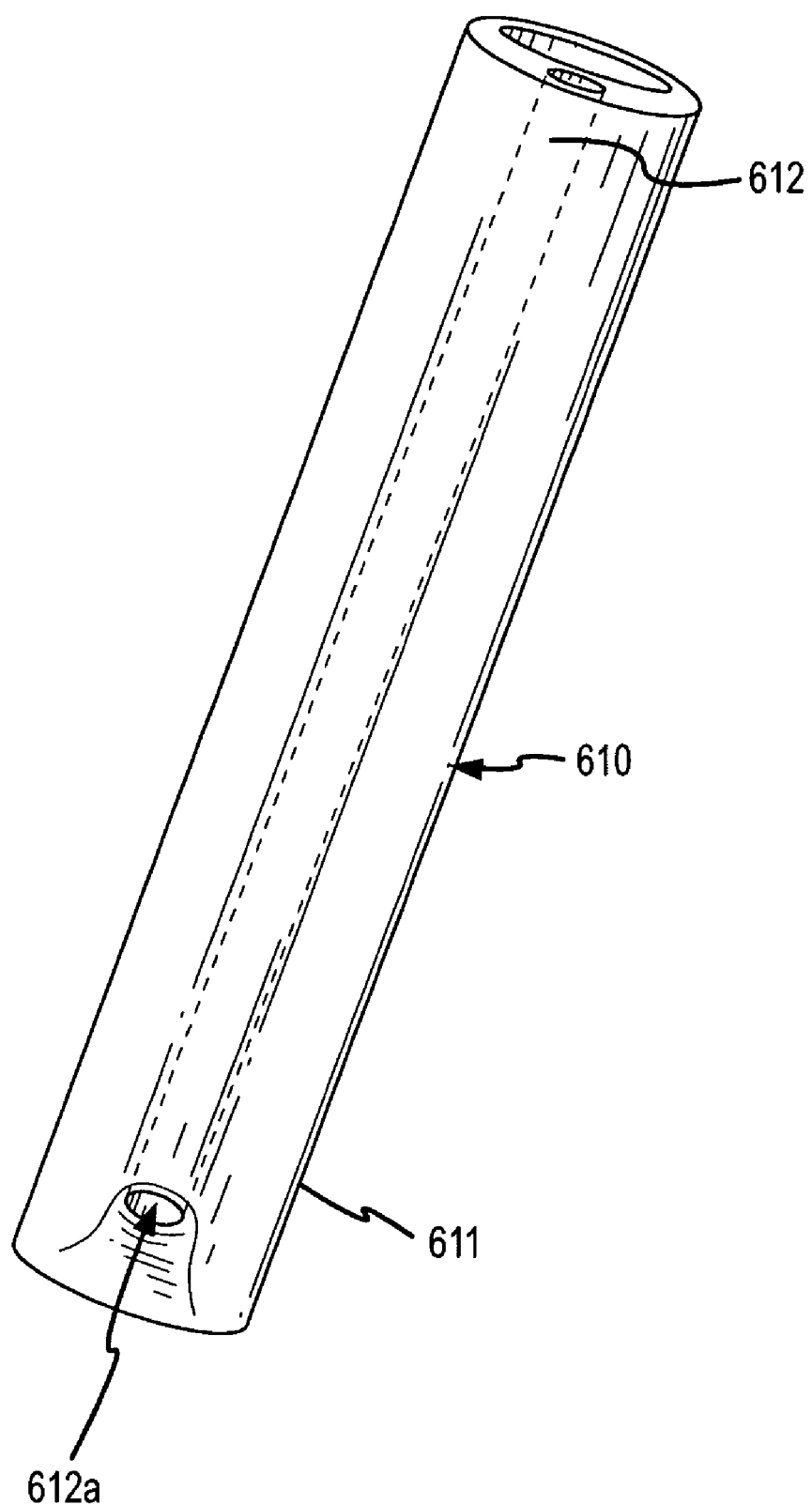
FIG. 6A illustrates a jacket sheath according to one embodiment of the present invention.
Figures 6B, 6C:
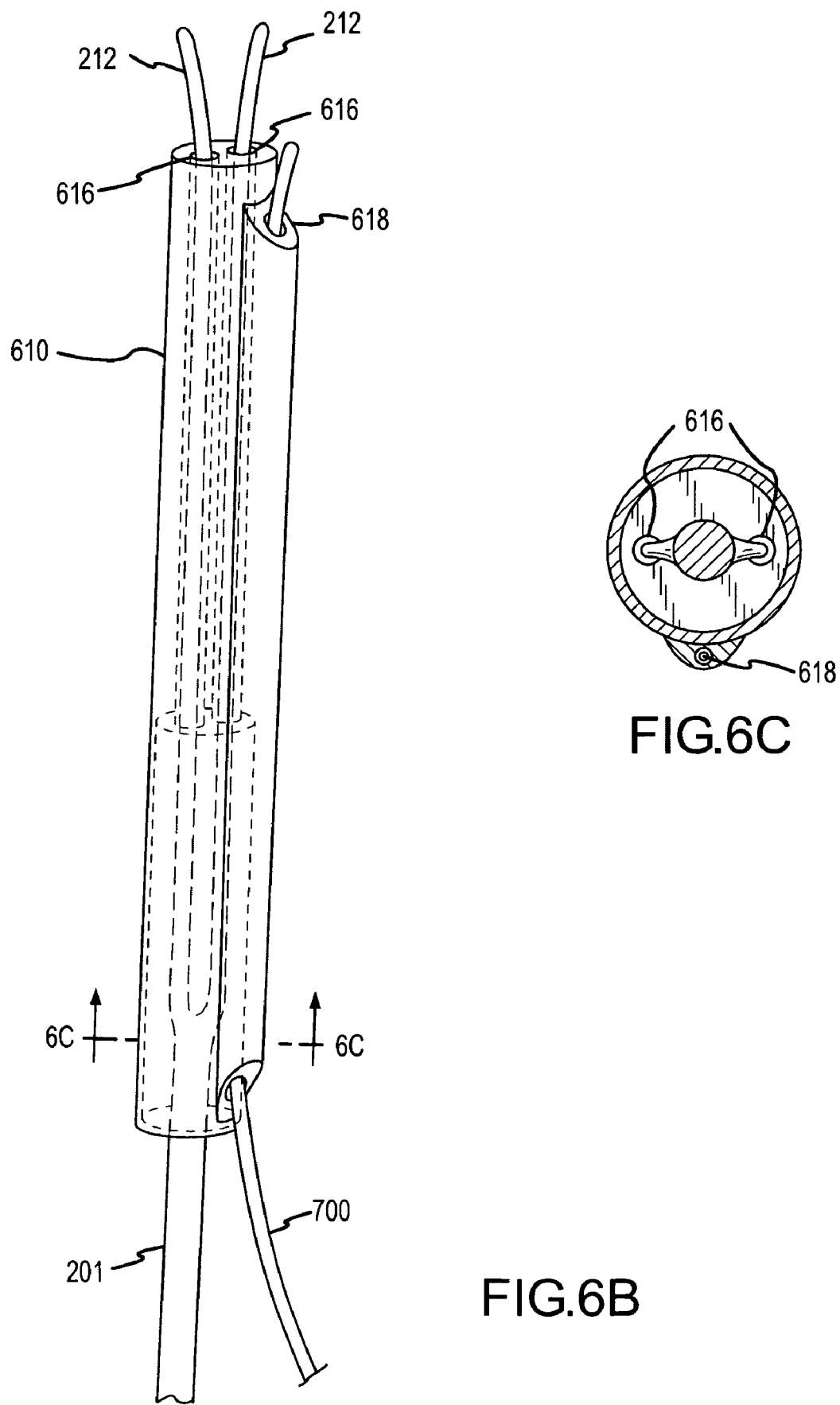
FIG. 6B illustrates a jacket sheath according to one embodiment of the present invention.
FIG. 6C illustrates a cut away view of a jacket sheath according to one embodiment of the present invention.

As shown in FIG. 6A, proximal end 611 of jacket sheath 610 may include an aperture 612a for receiving guide wire (not shown), such that a segment of guide wire is housed within the sheath 610. Here, guide 612 resides substantially within the cylindrical wall of jacket sheath 610. In the embodiment shown in FIGS. 6B and 6C, jacket sheath 610 includes two lumens 616 for housing distal extensions 212, and a lumen 618 for housing guide wire 700.

Figure 7A:
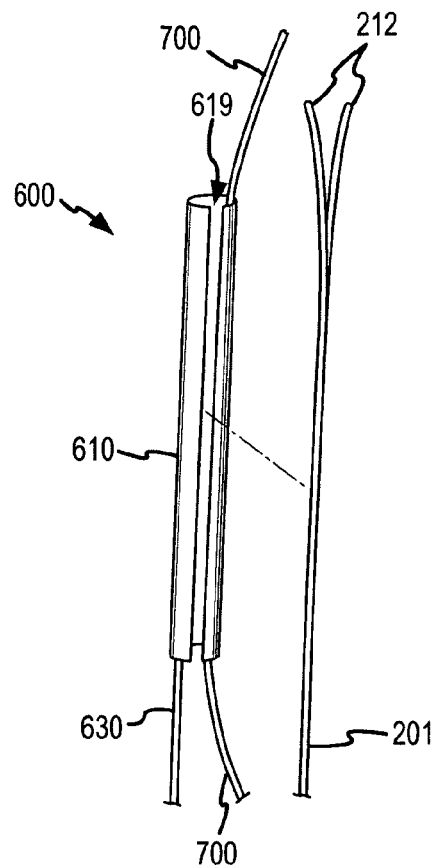
FIG. 7A illustrates a constraint assembly according to one embodiment of the present invention.
Figure 7B:
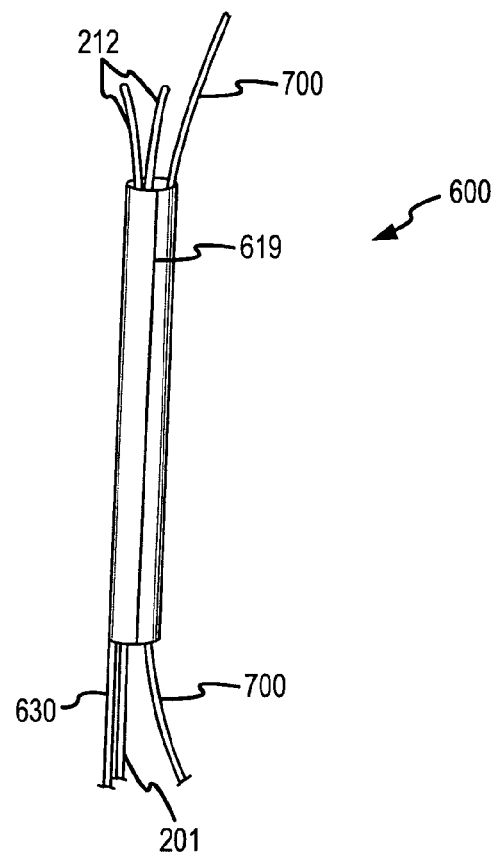
FIG. 7B illustrates a constraint assembly according to one embodiment of the present invention.
Figure 7C:
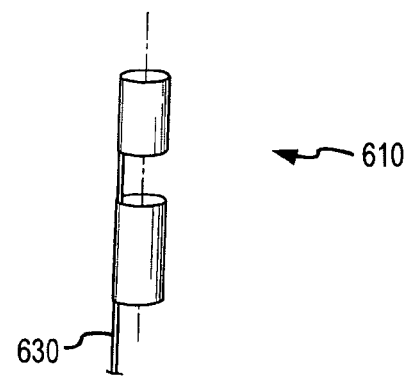
FIG. 7C illustrates a constraint assembly according to one embodiment of the present invention.

FIGS. 7A and B illustrate another embodiment of constraint assembly 600 which includes a split tube type of jacket sheath 610. Guide wire 700 may be passed through split 619, instead of being threaded through a monorail-type guide. Similarly, delivery catheter shaft 201 or guide catheters 300, 400 may be passed through split 619, thus allowing for easy removal and replacement of jacket sheath 610. As depicted in FIG. 7C, in some cases jacket sheath 610 may not be continuous, but instead may include multiple segments. Such a configuration can be advantageous by providing less material for introduction into the vasculature, thus diminishing the risk for clotting. Relatedly, by providing less luminal surface, the amount of friction between jacket sheath 610 and delivery catheter 200 or adjunctive catheter 300, 400.

Figure 8:
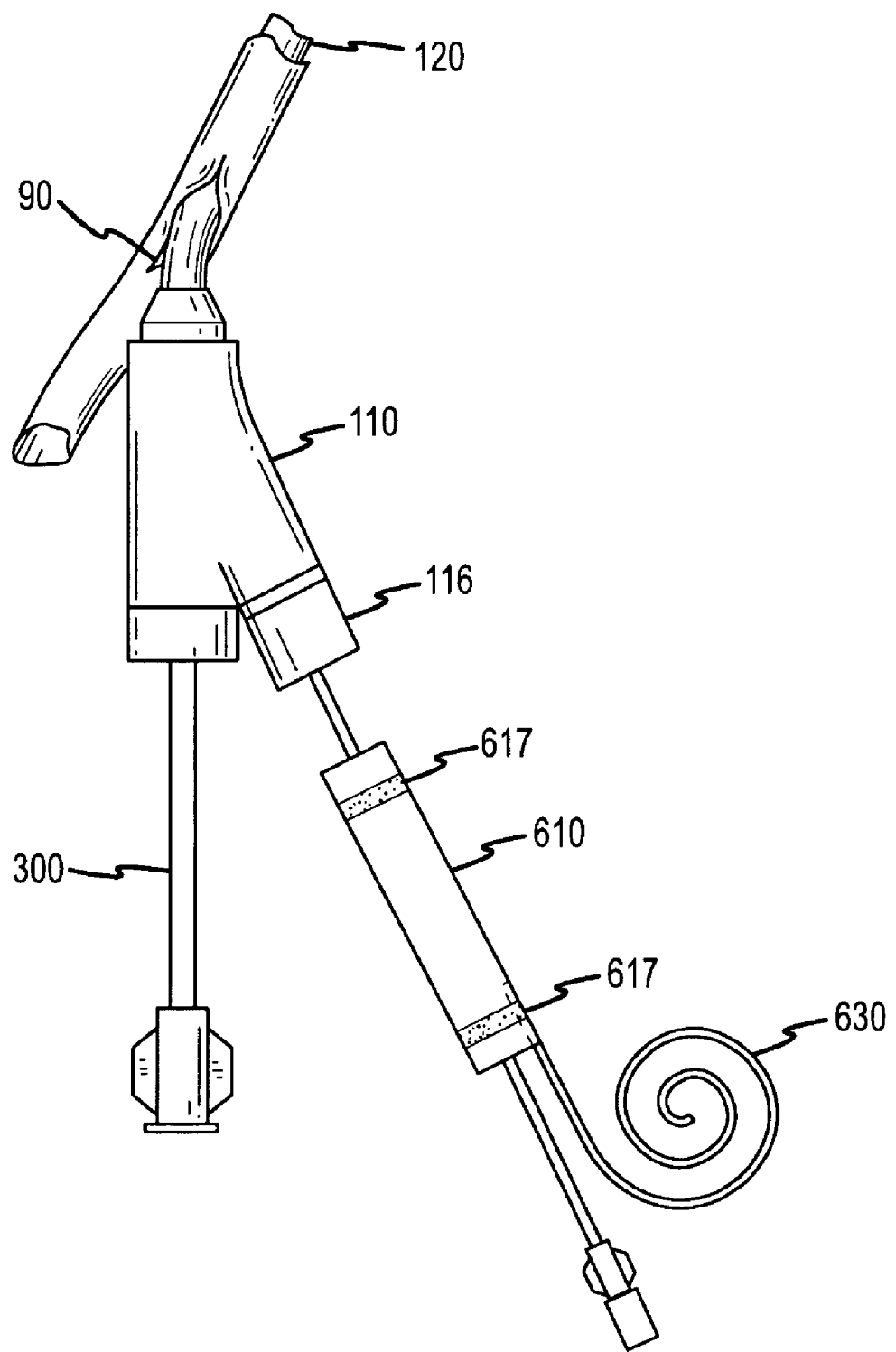
FIG. 8 illustrates an introducer assembly according to one embodiment of the present invention.

As seen in FIG. 8, jacket sheath 610 can be passed through first port 116 of Y-hub 110. Lead 630 can be manipulated by a physician to control movement of jacket sheath 610. By allowing jacket 610 to be fully retracted out of introducer sheath 120 and Y-hub 110, external to the patient's vessel entry 90, the functional diameter of device 10 remaining in the patient (e.g. catheters 200, 300, or 400) can be reduced. Often, jacket sheath can remain outside of the patient's body during the dwell period. Relatedly, larger diameter delivery catheters 200, adjunctive coronary catheters 300, or peripheral catheters 400 may be used in devices 10 having such fully retractable jackets 610. For the same reason, introducer sheaths 120 having smaller outside diameter may be used. Jacket sheath 610 may include markers 617 for position verification. In some embodiments, markers 617 may include radiopaque materials.

Figures 9A, 9B:
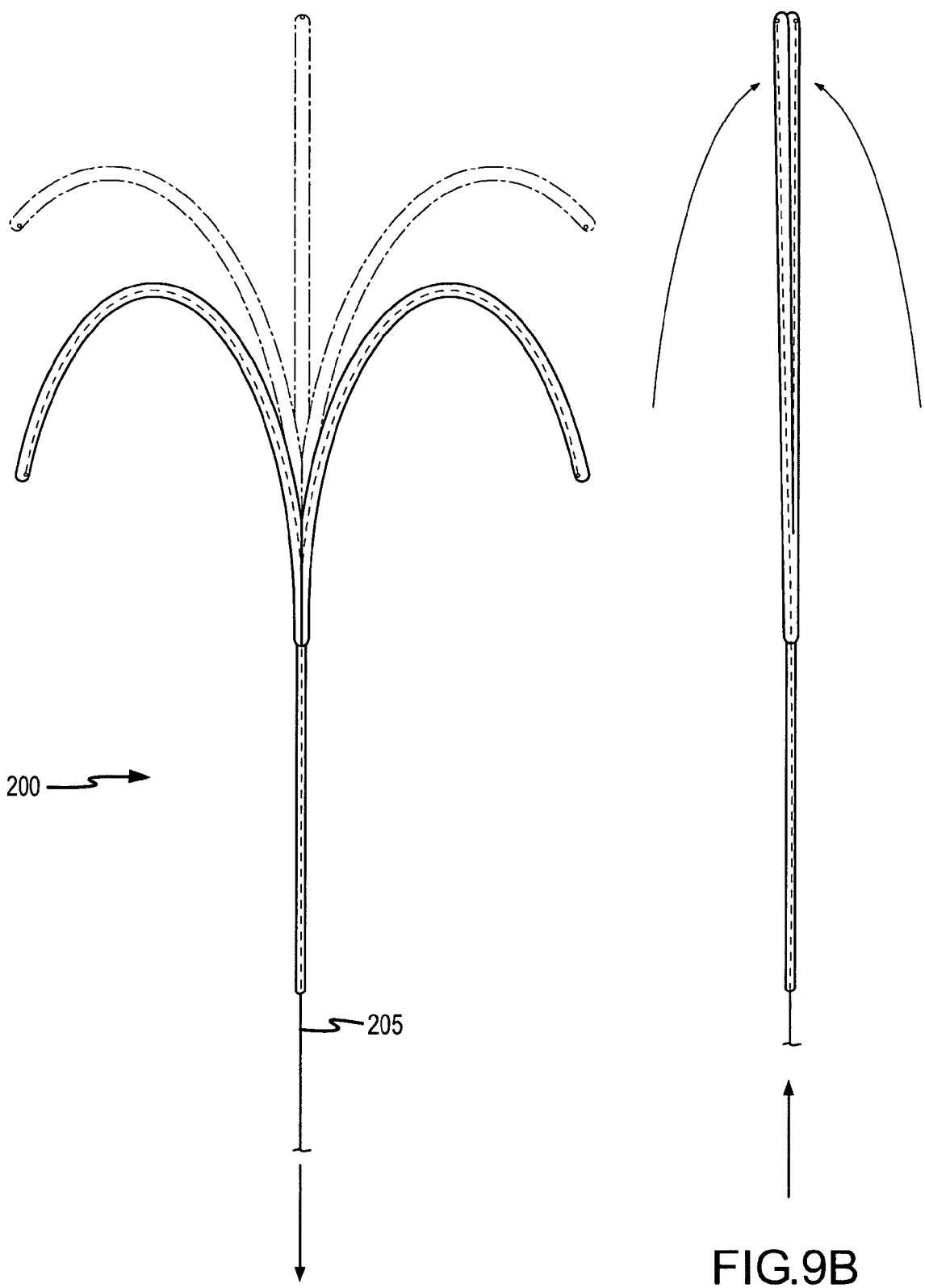
FIG. 9A illustrates a delivery catheter according to one embodiment of the present invention.
FIG. 9B illustrates a delivery catheter according to one embodiment of the present invention.

FIGS. 9A and 9B illustrate a variable shape distal arm design for delivery catheter 200. Catheter 200 may include a bifurcated pull wire 205 that can be affixed with the inside distal tips of distal extensions 212, on the side of each distal extension 212 that becomes the inside of the curve. Thus, when tension is put on pull wire 205, it effectively shortens the side of distal extension 212 it is attached to, causing it to bend. This deployed orientation, where distal extensions 212 are bent and separated from one another, is shown in FIG. 9A. Releasing pull wire 205 allows distal extensions 212 to go back to their default at-rest straight configuration. This collapsed orientation is shown in FIG. 9B.

Figure 10A:
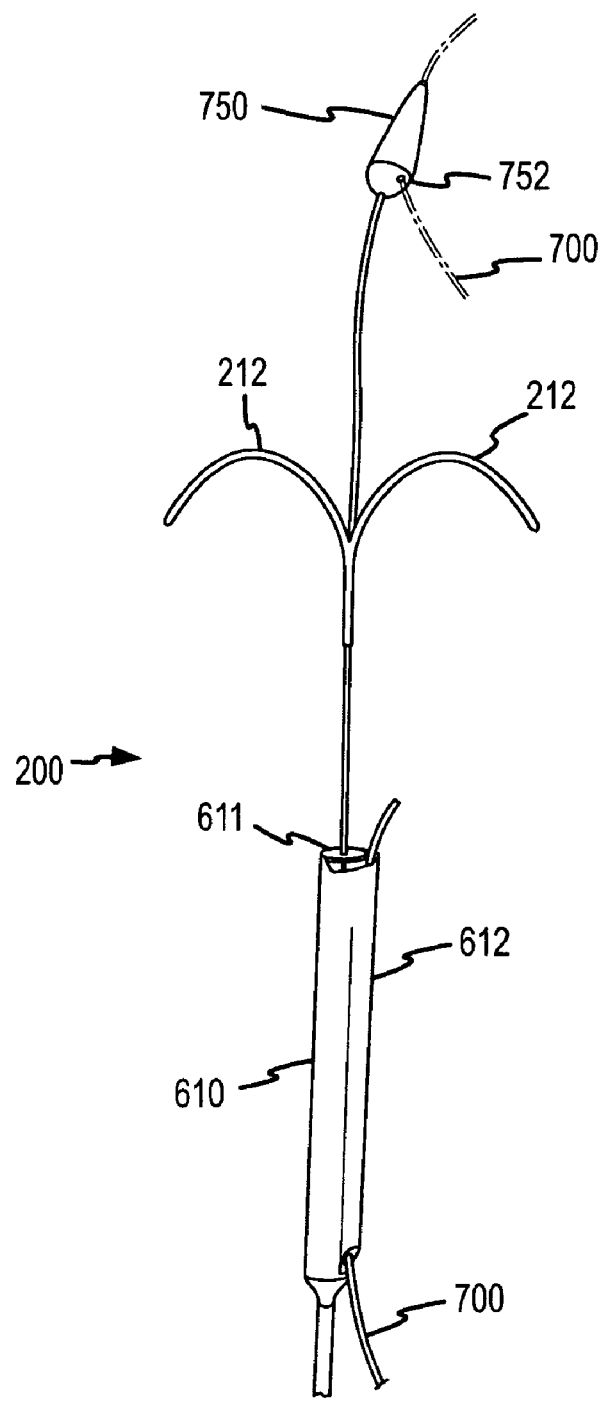
FIG. 10A illustrates a delivery catheter and constraint assembly according to one embodiment of the present invention.
Figure 10B:
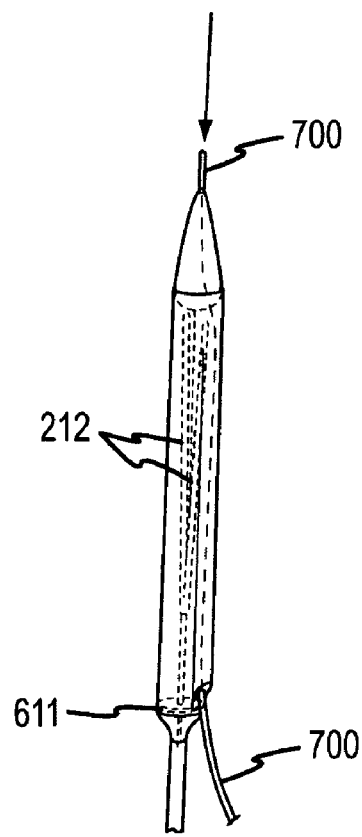
FIG. 10B illustrates a delivery catheter and constraint assembly according to one embodiment of the present invention.

FIGS. 10A and 10B illustrate another embodiment of the present invention, where delivery catheter 200 includes a tapered, atraumatic distal tip or cone 750, or other dilator means for maximizing the functional cross-section of a vessel prior to deployment delivery catheter 200. In some cases, distal tip 750 is not coupled with delivery catheter 200. In some cases, distal tip 750 may have a guide 752 such as a rail or a lumen which can be used in conjunction with guide wire 700. It will be appreciated that guide wire 700 can be a floppy-type wire, which can reduce the likelihood of tapered cone 750 creating a vessel perforation when advanced for distal catheter arm cannulation. The diameter of the guide wire may vary, although in many cases is it about 0.035 inches. FIG. 10A shows distal extensions 212 of delivery catheter 200 in a high-profile deployed configuration. Jacket sheath 610 may include a seal or gasket 611 which is mounted on or otherwise connected with catheter shaft 201, and therefore advances and retracts with delivery catheter shaft 201 advancement and retraction while remaining in sealed engagement with inner surface of jacket sheath 610. Here, gasket 611 is disposed toward the distal end of jacket sheath 610, and the proximal end of jacket sheath is otherwise sealed. Thus, jacket sheath 610 can be closed to blood flow when distal bifurcation 210 is in the deployed condition. FIG. 10B shows distal extensions 212 of delivery catheter 200 in a low-profile undeployed configuration. Here, gasket 611 is disposed toward the proximal end of jacket sheath 610, and distal cone 750 effectively seals the distal end of jacket sheath 610. By preventing blood from flowing through jacket sheath 610, gasket 610 can help reduce the risk of thrombus formation within sheath 610.

Figure 11:
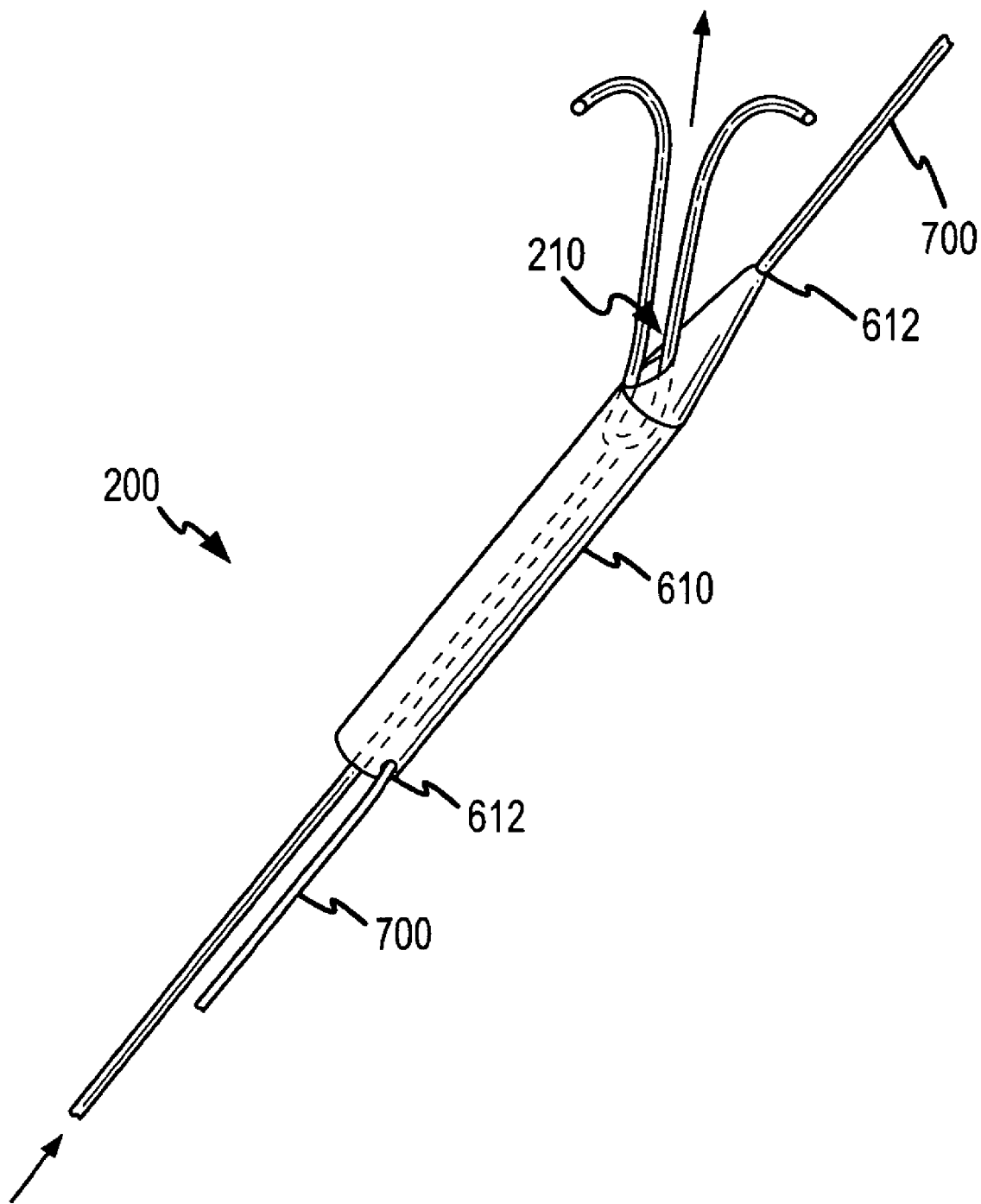
FIG. 11 illustrates a constraint assembly according to one embodiment of the present invention.

Cover jacket sheath 610 for constraining distal extensions 212 may be of multiple configurations, depending on the overall product needs. For example, jacket sheath 610 can accommodate a guide wire lumen or monorail-type arrangement. Further, jacket sheath 610 may be designed with tapers on each end or, as shown in FIG. 11, may be include an untapered proximal end and a tapered distal end. Here, a distal end of guide 612 exits at a central tip of jacket sheath 610, whereas distal bifurcation 210 exits lateral to the central tip. It is appreciated that distal bifurcation 210 can exit a single aperture, as shown here, or alternatively, distal bifurcation 210 can exit two apertures, whereby each of the two distal extensions 212 exits a different aperture. The two apertures can be on the same side of jacket sheath 610, or on different or opposite sides of sheath 610. Such configurations can provide less traumatic passage of delivery catheter 200 through the patient's vasculature.

The present invention provides a variety of approaches for preventing or inhibiting the formation of a blood clot or thrombus within jacket sheath 610, for example by avoiding the pooling of stagnant or static blood therein. In some cases, these approaches will include a jacket sheath 610 that remains integral with delivery catheter shaft 201. As shown in FIG. 12A, jacket sheath 610 can be in sealed cooperation with delivery catheter shaft 201 so as to prevent blood from flowing into or through sheath 610. Gasket 611 can prevent blood infusion, or infusate seepage, at the distal end of jacket sheath 610, and the proximal end of sheath 610 may be otherwise sealed with shaft 201. Gasket 611 can be fixed with shaft 201, and in sealed engagement with the inner surface of jacket sheath 610. FIG. 12B illustrates delivery catheter shaft 200 having a port 206 in fluid communication with interior of jacket sheath 610. Port 206 can be used to deliver infusate from delivery catheter shaft 201 to sheath 610. By allowing infusate to fill the luminal space or effective cavity of jacket sheath 610, a positive infusate flow into this cavity can be created, so as to prevent or inhibit thrombus formation. Similarly, the interior chamber of jacket sheath 610 can be pressurized with the infusate from port 206. Often, jacket sheath 610 will be sealed with one or more gaskets or seals 611 so as to prevent blood infusion or infusate seepage. A positive pressure of an effective reservoir of infusate can build up in the cavity remaining in jacket sheath 610. Because there is a slight pressure (greater than blood pressure), the blood cannot so easily displace the infusate in the cavity, and thus it prevents clotting. In a nonsealed or open version as seen in FIG. 12C, jacket sheath 610 may include proximal end vents or perforations 613 so as to allow continuous blood flow through jacket sheath 610. Here, incoming blood perfuses out of sheath 610 via fenestrations, slots, or other openings 613 in jacket sheath 610.

Figure 13:
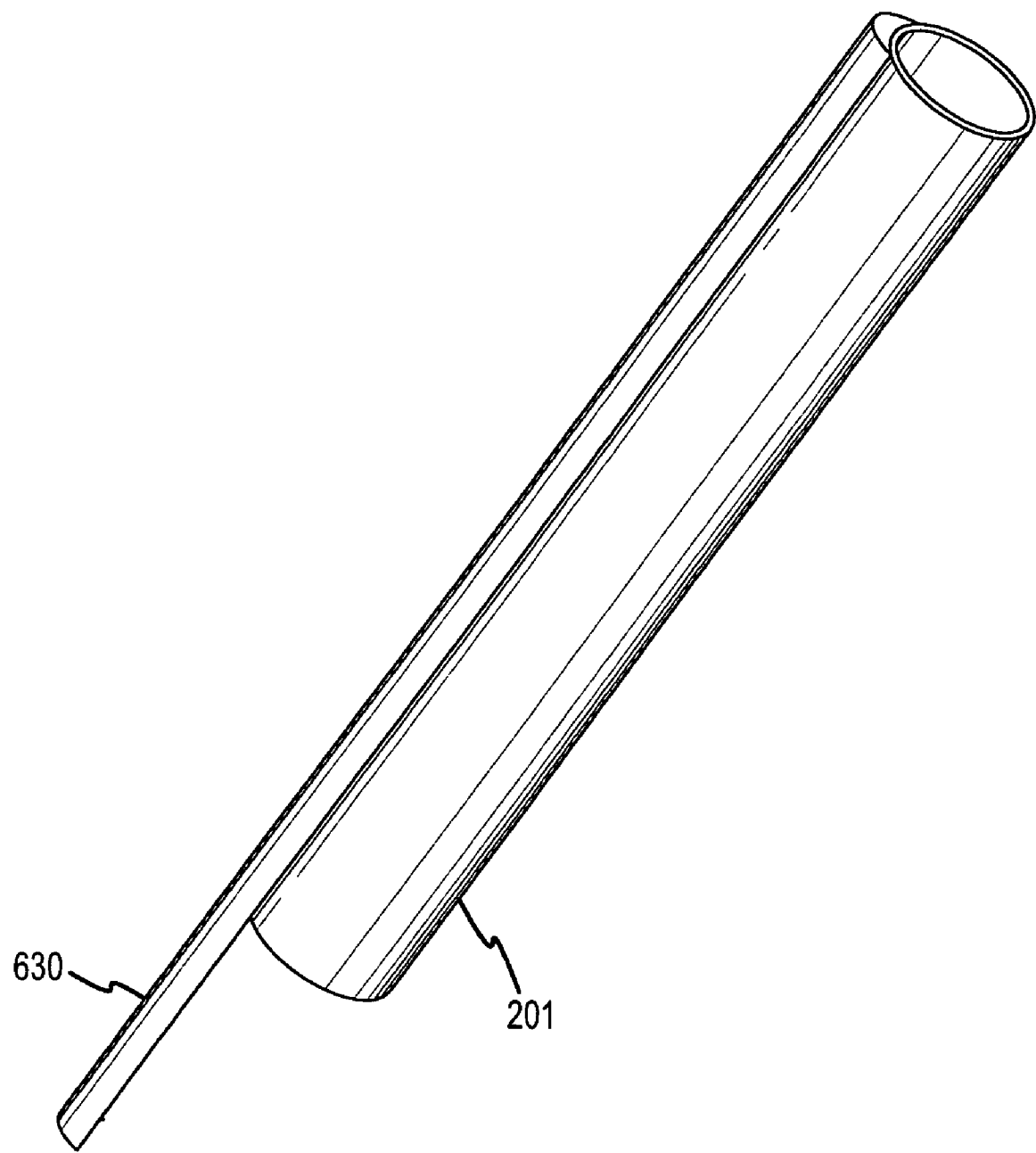
FIG. 13 illustrates a constraint assembly according to one embodiment of the present invention.

FIG. 13 illustrates a partial view of delivery catheter shaft 201 according to one embodiment of the present invention. Lead 630 is shaped in a semi-circle or modified "D" shape, and nests with delivery catheter shaft 201, thus providing facile passage through introducer sheath (not shown). It is appreciated that lead 630 can have any of a variety of shapes, and many times will be configured so as to minimize the geometry or the overall functional diameter (or functional cross-sectional area) of the lead 630 and delivery catheter shaft 201 combination. In a related embodiment, lead 630 can be a semi-ridged tube made of polymer or metal that travels along the length of the delivery catheter shaft 201 as a rail type system. In this sense, a modified "D" shape can be useful where there is limited need for torque to be applied to lead 630, but lead 630 still needs to withstand compression and tension forces associated with advancement and retraction of jacket sheath 610.

Figure 14A:
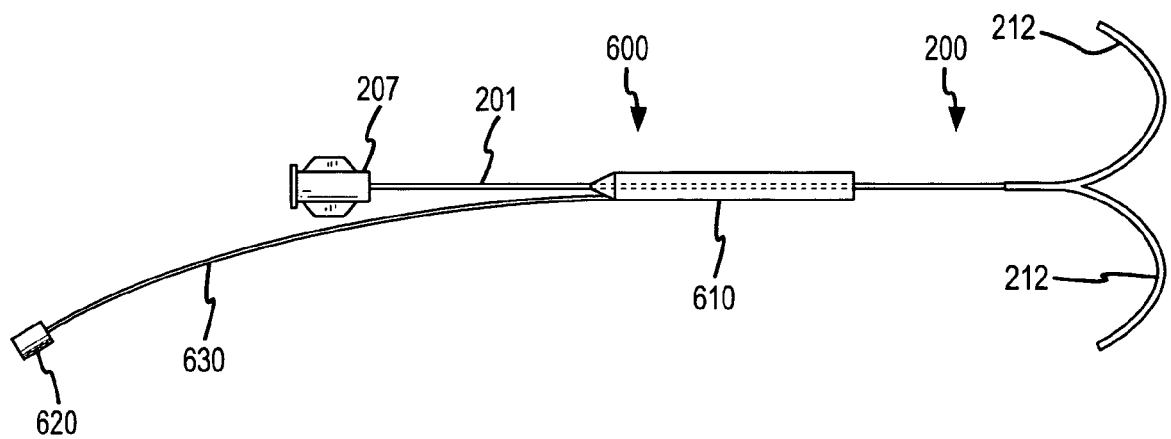
FIG. 14A illustrates a delivery catheter and constraint assembly according to one embodiment of the present invention.
Figure 14B:
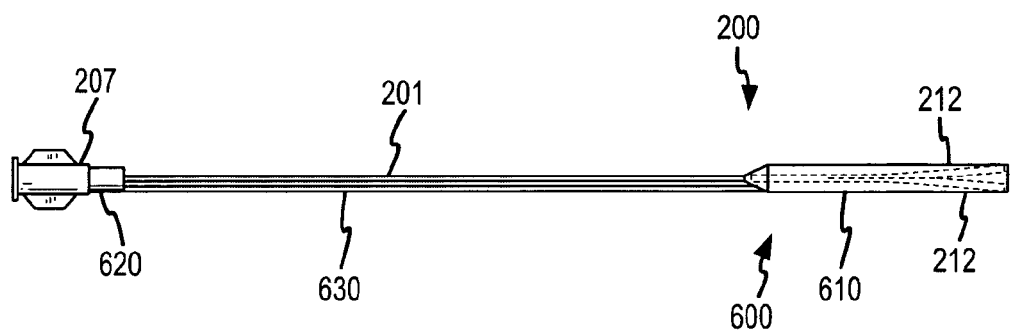
FIG. 14B illustrates a delivery catheter and constraint assembly according to one embodiment of the present invention.

FIGS. 14A and 14B illustrates a constraint assembly 600 and delivery catheter 200 according to one embodiment of the present invention. FIG. 14A shows constraint assembly 600 is a retracted position, such that distal extensions 212 of delivery catheter 200 are in a deployed orientation. FIG. 14B shows constraint assembly 600 in an advanced position, such that distal extensions 212 of delivery catheter 200 are in an undeployed orientation. Constraint assembly 600 can be fixed in the advanced position by locking or otherwise removably coupling connector 620 with a clamp 207 of delivery catheter 200. In some cases, all components of constraint assembly 600 (e.g. handle 620, lead 630, and sheath jacket 610) can be constructed so as to allow easy advancement through Y-hub 110 (not shown here), and along guide wire 700 (not shown here).

Figure 15A:
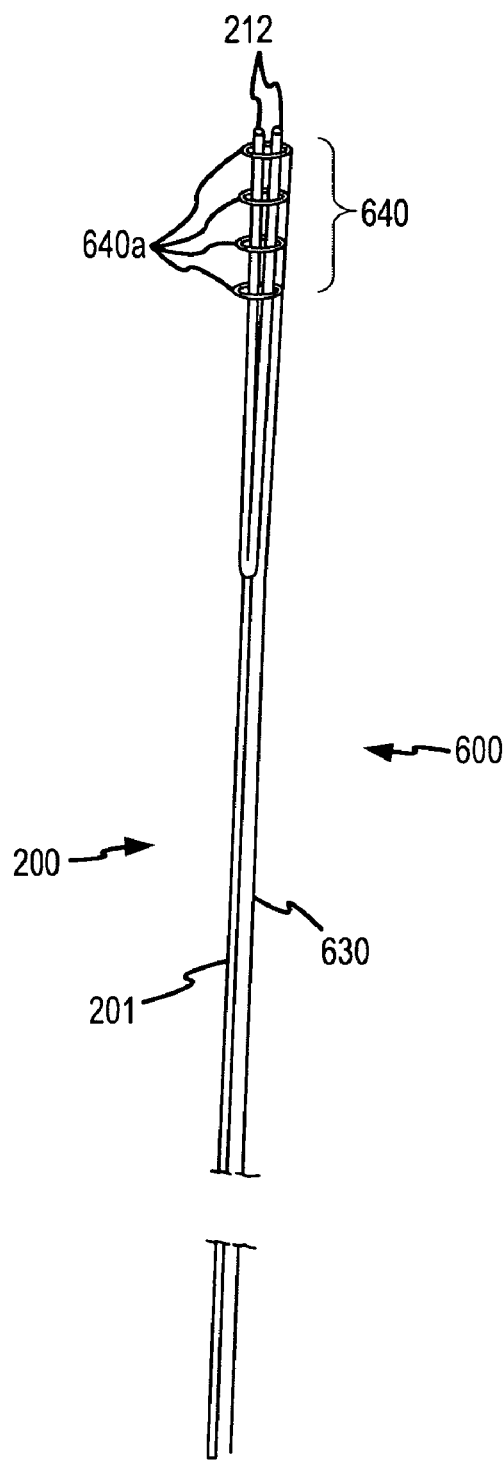
FIG. 15A illustrates a delivery catheter and constraint assembly according to one embodiment of the present invention.
Figure 15B:
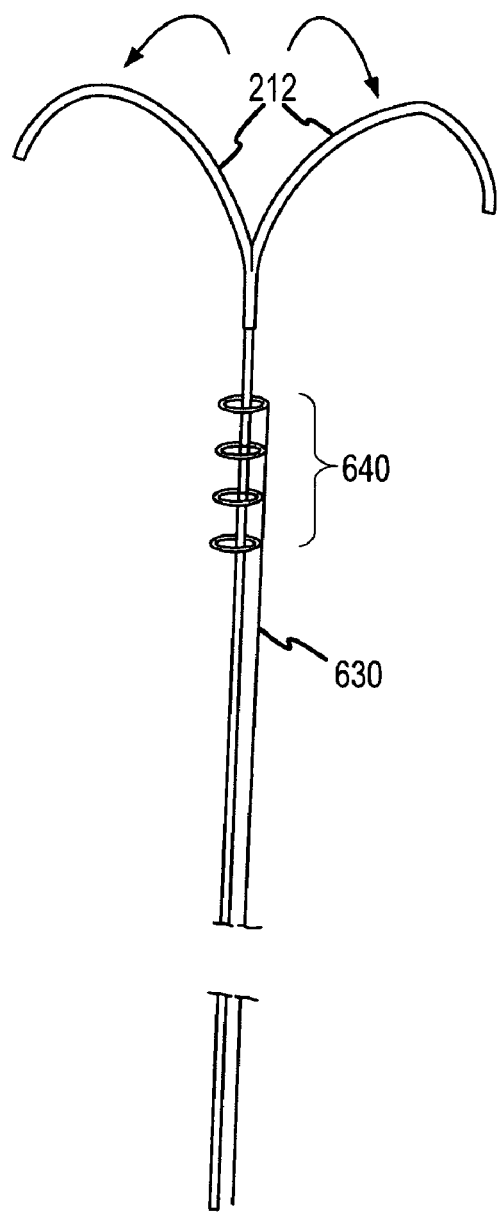
FIG. 15B illustrates a delivery catheter and constraint assembly according to one embodiment of the present invention.

FIGS. 15A and 15B illustrate a constraint assembly 600 and delivery catheter 200 according to one embodiment of the present invention. Constraint assembly 600 includes a collapsible ring capture system 640 that includes a plurality of rings 640a configured to slidingly engage delivery catheter 200 in a coaxial fashion. Connector 630 may be coupled with one or more rings 640a of collapsible ring capture system 640. FIG. 15A shows constraint assembly 600 in an advanced position, such that distal extensions 212 of delivery catheter 200 are in an undeployed configuration. FIG. 15B shows constraint assembly 600 in a retracted position, such that distal extensions 212 of delivery catheter 200 are in a deployed configuration. When connector 630 is retracted, rings 640a slide onto catheter hypotube or shaft 201, thus allowing distal extensions 212 to snap into their open configuration. Rings 640a can be designed such that once they are retracted onto hypotube or shaft 201, they collapse onto the surface of hypotube 201 to optimize the functional cross sectional area of the vessel.

Figures 16A, 16B:
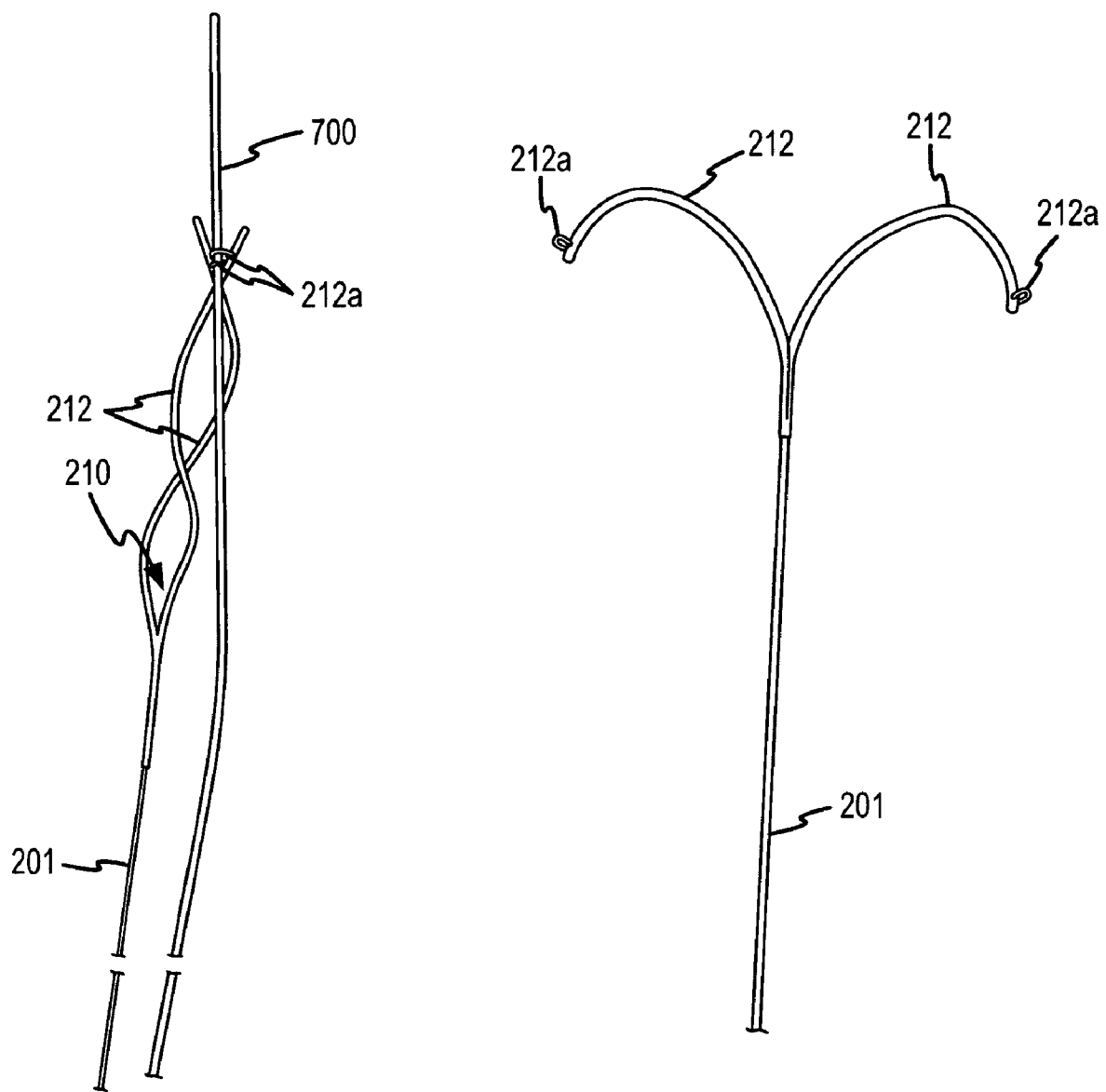
FIG. 16A illustrates a delivery catheter and constraint assembly according to one embodiment of the present invention.
FIG. 16B illustrates a delivery catheter and constraint assembly according to one embodiment of the present invention.

FIGS. 16A and 16B illustrate a means for providing constrained advancement of delivery catheter 200 to the renal ostia or other deployment locations, according to one embodiment of the present invention. FIG. 16A shows distal bifurcation 210 in a restrained position. Each distal extension 212 of distal bifurcation 210 includes a guide wire ring 212a coupled therewith, such that guide wire rings 212a are in slidable cooperation with guide wire 700. Guide wire rings 212a may be disposed at or near the distal tips of distal extensions 212, or at any location along the length of distal extensions 212. When distal bifurcation 210 is placed in an axially constrained state, such that distal extensions 212 are more or less aligned or parallel to one another, rings 212a can be aligned, such that guide wire 700 may be placed through rings 212a, thus holding distal extensions 212 together. In some embodiments, guide wire 700 may be a 0.035" diameter guide wire. As seen in FIG. 16B, when delivery catheter 200 is placed in position at or about a deployment location such as the renal arteries, guide wire 700 may be withdrawn, allowing distal extensions 212 to move toward their deployed orientation. Cannulation of the renal arteries can be achieved in the manner described in previously incorporated U.S. patent application Ser. No. 11/084,738.

Figure 17A:
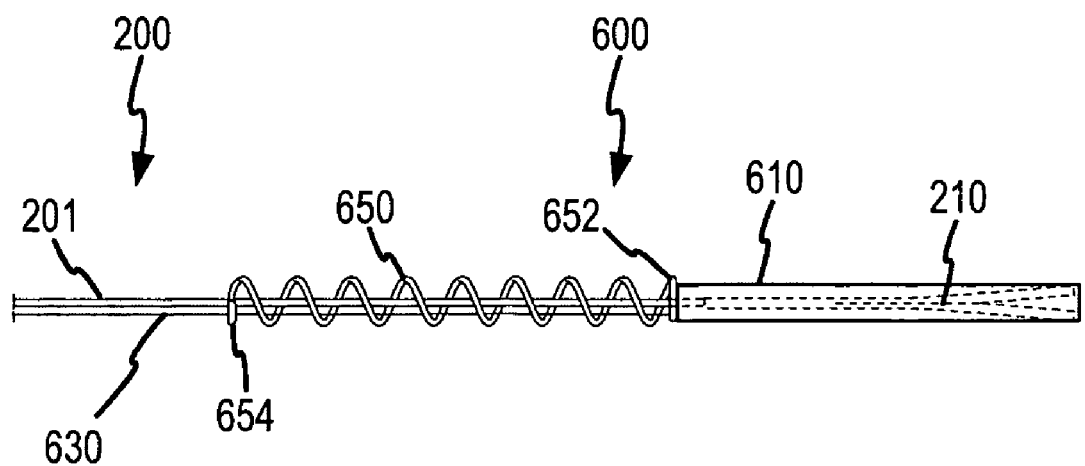
FIG. 17A illustrates a delivery catheter and constraint assembly according to one embodiment of the present invention.
Figure 17B:
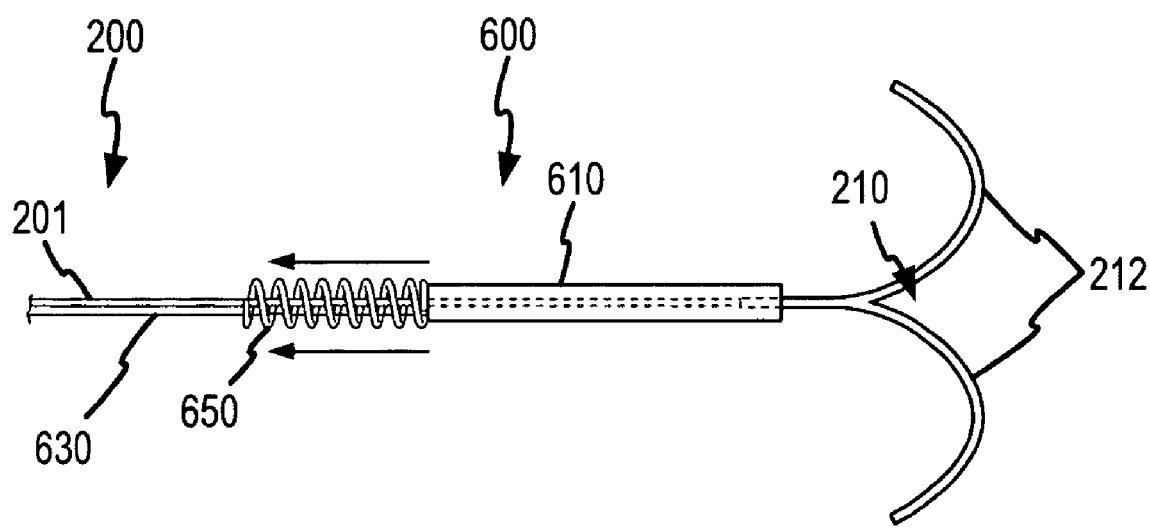
FIG. 17B illustrates a delivery catheter and constraint assembly according to one embodiment of the present invention.

FIGS. 17A and 17B illustrate a means for providing constrained advancement of delivery catheter 200 to the perirenal aorta or other deployment locations, according to one embodiment of the present invention. FIG. 17A shows distal bifurcation 210 in a restrained orientation. Constraint assembly 600 includes a spring 650, where a spring distal end 652 is coupled with jacket sheath 610, and a spring proximal end 654 is coupled with delivery catheter shaft 201. Here, spring 650 is in a relaxed state, and jacket sheath 610 remains disposed distally along delivery catheter shaft 201 so as to constrain distal extensions 212 in a collapsed configuration. After insertion and deployment, spring-loaded jacket 610 can allow distal extensions 212 to be easily recaptured for withdrawal, by releasing tension in lead 630 to relax spring 650. FIG. 17B shows distal bifurcation 210 in a deployed configuration. When delivery catheter 200 is placed in the desired deployment location, for example in the aorta, lead 630 can be actuated so as to retract jacket sheath 610 and compress spring 650, thereby allowing distal extensions 212 to open, for example, against the aortic walls.

As noted previously, embodiments that include a delivery catheter shaft or hypotube 201 in combination with wire-type lead 630 (shown in FIG. 5A) can often provide a smaller profile or functional cross-section diameter than embodiments that include a delivery catheter shaft or hypotube 201 in combination with coaxial sleeve tube-type lead 630 (shown in FIG. 3A). It is appreciated that in some instances a coaxial connector sleeve tube-type lead 630 may be useful where a substantial pushing motion or compressive force is required to advance jacket sheath 610 over deployed distal extensions 212 in order to return distal bifurcation 210 to a constrained orientation. Yet the present inventors have discovered that the use of a spring-loaded jacket sheath 610 as described above can remove or reduce the need to push on lead 630 to apply a compressive force to sheath 610. Relatedly, spring 650 or a similar spring-like means can provide a constant compressive load on catheter shaft 201, and a constant tensile load on lead 630. Shaft 201 and/or lead 630 can be appropriately relatively sized to one another as desired. Often, the spring force and friction required to unsheathe and resheath distal extensions 212 can determine the compressive and tensile loads on shaft 201 and lead 630, respectively, and these factors may determine their relative sizes. In some cases, delivery catheter hypotube or shaft 201 outer diameter (OD) can be in a range between about 1 French and about 3 French. In some cases, the lead 630 diameter can be in a range between about 0.010 and about 0.025", sized appropriately for delivery catheter hypotube 201.

Figure 18:
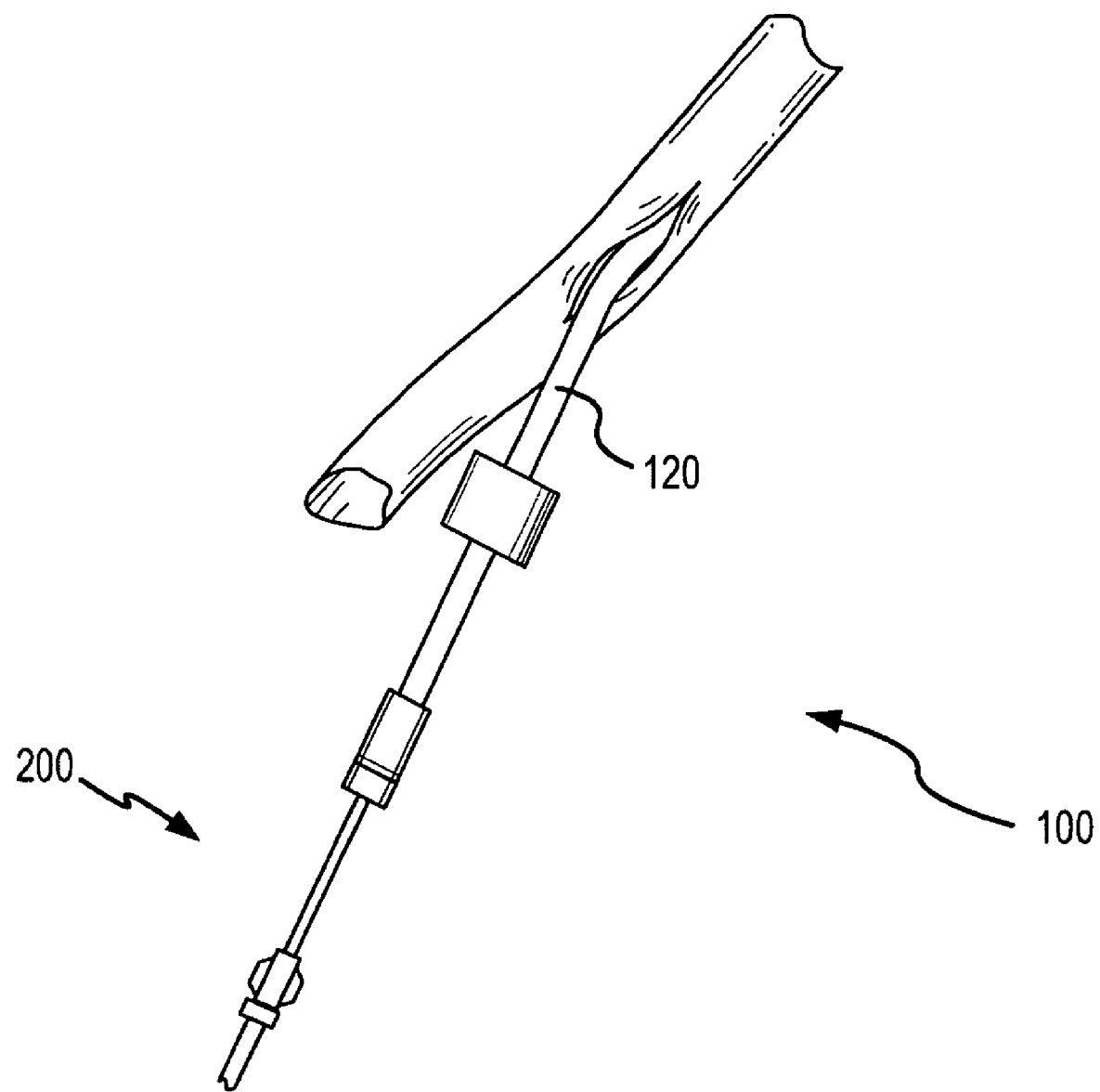
FIG. 18 illustrates an introducer assembly according to one embodiment of the present invention.

The present invention is also well suited for use with stand-alone delivery catheter systems that do not include a guide catheter. As seen in FIG. 18, device 10 includes a delivery catheter 200 configured to pass through introducer assembly 100, which includes introducer sheath 120, but not Y-hub 110. This configuration may be useful in situations where a secondary adjunctive catheter 300, 400 is not needed, and thus a lower overall profile can be achieved with such a stand-alone system.

While the above provides a full and complete disclosure of certain embodiments of the present invention, various modifications, alternate constructions and equivalents may be employed as desired. Therefore, the above description and illustrations should not be construed as limiting the invention, which is defined by the appended claims.

What is claimed is:

1. A method for positioning a delivery catheter in the renal arteries, the method comprising:
positioning an introducer sheath in an iliac artery;
advancing a renal delivery catheter having a distal bifurcation through the introducer sheath;
constraining the distal bifurcation in a low-profile configuration with a constraint assembly while advancing the distal bifurcation and the constraint assembly through the introducer sheath;
advancing the constrained distal bifurcation and the constraint assembly from the introducer sheath toward the renal arteries while the bifurcation remains constrained by the constraint assembly, such that the distal bifurcation and the constraint assembly move relative to the introducer sheath;
releasing the distal bifurcation from the constrained low-profile configuration to allow entry of a first distal extension of the distal bifurcation into one of the renal arteries and a second distal extension of the distal bifurcation into the other renal artery, wherein the first distal extension comprises a first lumen and a first distal aperture, and the second distal extension comprises a second lumen and a second distal aperture; and
delivering a fluid agent through the first and second distal extension lumens and the first and second distal apertures, respectively, such that the fluid agent flows into blood flowing within the renal arteries and feeds downstream into the kidneys via the renal arteries.

2. The method of claim 1, wherein the constraint assembly comprises a sheath, and constraining the distal bifurcation in the low-profile configuration comprises constraining the distal bifurcation with the sheath.

3. The method of claim 2, wherein passing the constrained distal bifurcation from the introducer sheath toward the renal arteries comprises advancing the sheath over a guide wire.

4. The method of claim 1, wherein the constraint assembly comprises a ring capture system, and constraining the distal bifurcation in the low-profile configuration comprises constraining the distal bifurcation with the ring capture system.

5. The method of claim 4, wherein passing the constrained distal bifurcation from the introducer sheath toward the renal arteries comprises advancing the ring capture system along a guide wire.

6. The method of claim 1, wherein the constraint assembly comprises a guide wire ring, and constraining the distal bifurcation in the low-profile configuration comprises constraining the distal bifurcation with the guide wire ring.

7. The method of claim 6, wherein passing the constrained distal bifurcation from the introducer sheath toward the renal arteries comprises advancing the guide wire ring along a guidewire.

8. The method of claim 1, further comprising advancing a second catheter through the introducer sheath.

9. The method of claim 8, further comprising performing a diagnostic or interventional procedure with the second catheter.

10. A method of positioning a delivery catheter in a first branch lumen and a second branch lumen, each branch lumen extending from a main lumen in a body of a patient, the method comprising:
positioning an introducer sheath in the main lumen;
advancing a delivery catheter having a distal bifurcation through the introducer sheath, wherein the distal bifurcation comprises a first distal extension having a first lumen and a first distal aperture, and a second distal extension having a second lumen and a second distal aperture;
constraining the distal bifurcation in a low-profile configuration while advancing the distal bifurcation through the introducer sheath;
advancing the constrained distal bifurcation from the introducer sheath toward the first branch lumen and the second branch lumen; and
releasing the distal bifurcation from the constrained low-profile configuration to allow entry of the first distal extension of the distal bifurcation into the first branch lumen and entry of the second distal extension of the distal bifurcation into the second branch lumen, while allowing blood flow within the patient from an upstream location in the main lumen, past each of the first and second branch lumens, to a downstream location in the main lumen;
wherein advancing the constrained distal bifurcation comprises advancing the introducer sheath through a puncture in a first femoral artery of the patient, and further comprises advancing a guide catheter through the introducer sheath and into a second femoral artery of the patient via the aortic bifurcation.

11. The method of claim 10, wherein constraining the distal bifurcation is performed using a constraint assembly comprising a member selected from the group consisting of a sheath, a ring capture system, and a guide wire ring.

* * * * *